(12) United States Patent
Andree et al.

(10) Patent No.: US 6,339,044 B1
(45) Date of Patent: *Jan. 15, 2002

(54) N-P-CYANOARYL NITROGEN-CONTAINING HETEROCYCLES HAVING PENDENT SULFUR-CONTAINING GROUPS

(75) Inventors: Roland Andree; Mark Wilhelm Drewes, both of Langenfeld; Hans-Joachim Santel; Markus Dollinger, both of Leverkusen; Christoph Erdelen, Leichlingen, all of (DE)

(73) Assignee: Bayer Aktiengesellschaft, Leverkusen, DEX ( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/049,447

(22) Filed: Mar. 27, 1998

Related U.S. Application Data

(63) Continuation of application No. 08/656,293, filed as application No. PCT/EP94/04070 on Dec. 7, 1994, now abandoned.

(30) Foreign Application Priority Data

Dec. 20, 1993 (DE) .................................. P 43 43 451
Jul. 11, 1994 (DE) .................................. P 44 24 401

(51) Int. Cl.$^7$ ................... C07D 239/54; A01N 43/54
(52) U.S. Cl. ................... 504/240; 504/243; 504/219; 504/221; 544/285; 544/238; 544/311; 544/312; 544/253
(58) Field of Search .................. 504/240, 243; 514/259, 269, 274; 544/285, 309, 311, 314

(56) References Cited

U.S. PATENT DOCUMENTS

| | | | |
|---|---|---|---|
| 5,084,084 A | * | 1/1992 | Satow et al. ............... 544/310 |
| 5,356,863 A | * | 10/1994 | Satow et al. ............... 504/243 |
| 5,593,945 A | * | 1/1997 | Andree et al. ............. 504/243 |
| 5,681,794 A | * | 10/1997 | Andree et al. ............. 504/243 |

FOREIGN PATENT DOCUMENTS

WO   WO 92/11244   *   7/1992   ................. 504/243

OTHER PUBLICATIONS

Copy of WO 92/11244 is not being sent with the action because this reference was cited by the applicants in the parent 08/656,293.*

* cited by examiner

Primary Examiner—John M. Ford
(74) Attorney, Agent, or Firm—Norris McLaughlin & Marcus

(57) ABSTRACT

N-Cyanoaryl nitrogen heterocycles having sulfur-containing groups of the formula (1),

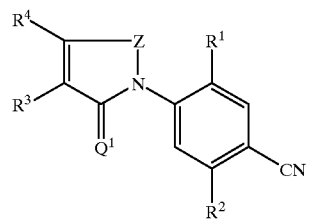

(I)

in which $Q^1$ represents oxygen or sulfur, $R^1$ represents hydrogen or halogen, $R^2$ represents halogen, cyano, nitro, amino or the grouping —N($A^1$)$SO^2$A, in which A represents, in each case, optionally substituted alkyl, alkenyl, alkinyl, dialkylamino, cycloalkyl, cycloalkylalkyl, aryl or arylalkyl, and $A^1$ represents hydrogen, formyl or, in each case optionally substituted, alkyl, alkenyl, alkinyl, alkylcarbonyl, alkoxycarbonyl or alkylsulphonyl, or together with A represents alkanediyl, $R^3$ represents hydrogen, halogen, cyano or optionally substituted alkyl, $R^4$ represents optionally substituted alkyl or together with $R^3$ represents alkanediyl, and Z represents one of the groups

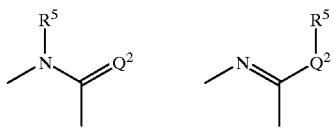

in which $Q^2$ represents oxygen or sulfur and $R^5$ represents hydrogen or, in each case optionally substituted, alkyl, alkenyl, alkinyl or alkylcarbonyl, and salts of compounds of the formula (1)

with the proviso that at least one of the groupings $Q^1$ or $Q^2$ represents sulfur.

Several processes are disclosed for preparing these compounds which are useful as herbicides and insecticides.

13 Claims, No Drawings

N-P-CYANOARYL NITROGEN-CONTAINING HETEROCYCLES HAVING PENDENT SULFUR-CONTAINING GROUPS

This is a continuation of application Ser. No. 08/656,293, filed on Jun. 13, 1996, now abandoned, which is a 371 of PCT/EP94/04070 filed on Dec. 7, 1994.

The invention relates to novel N-cyanoaryl nitrogen heterocycles having sulphur-containing groupings, a plurality of processes for their preparation and their use as herbicides and insecticides.

It is already known that certain N-cyanoaryl nitrogen heterocycles have herbicidal properties (cf. WO-A 91/00278, WO-A 92/11244, EP-A 408382, EP-A 438209, EP-A 473551, DE-A 4237920). However, the herbicidal action and the compatibility of the previously known N-cyanoaryl nitrogen heterocycles with cultivated plants are not entirely satisfactory.

The novel N-cyanoaryl nitrogen heterocycles having sulphur-containing groupings of the general formula (I) have now been found,

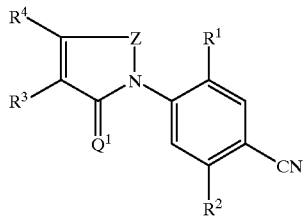

(I)

in which
Q$^1$ represents oxygen or sulphur,
R$^1$ represents hydrogen or halogen,
R$^2$ represents halogen, cyano, nitro, amino or the grouping —N(A$^1$)SO$_2$A, in which
  A represents, in each case, optionally substituted alkyl, alkenyl, alkinyl, dialkylamino, cycloalkyl, cycloalkylalkyl, aryl or arylalkyl, and
  A$^1$ represents hydrogen, formyl or, in each case optionally substituted, alkyl, alkenyl, alkinyl, alkylcarbonyl, alkoxycarbonyl or alkylsulphonyl, or together with A represents alkanediyl,
R$^3$ represents hydrogen, halogen, cyano or optionally substituted alkyl,
R$^4$ represents optionally substituted alkyl or together with R$^3$ represents alkanediyl, and
Z represents one of the groupings below

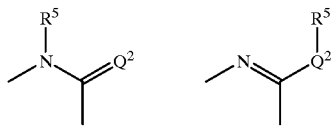

in which
Q$^2$ represents oxygen or sulphur and
R$^5$ represents hydrogen or, in each case optionally substituted, alkyl, alkenyl, alkinyl or alkylcarbonyl,
and salts of compounds of the formula (I)
with the proviso that at least one of the groupings Q$^1$ or Q$^2$ represents sulphur.

The general formula (I) therefore represents the isomeric compounds of the general formulae (IA) and (IB) below

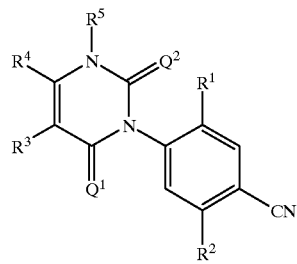

(IA)

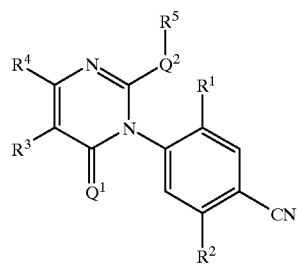

(IB)

The novel N-cyanoaryl nitrogen heterocycles having sulphur-containing groupings of the general formula (I) are obtained if (a) aminoalkenoic (thio)esters of the general formula (II)

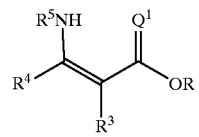

(II)

in which
Q$^1$, R$^3$, R$^4$ and R$^5$ have the meanings given above and
R represents alkyl,
are reacted with cyanoaryl iso(thio)cyanates of the general formula (III)

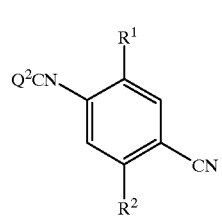

(III)

in which
Q$^2$, R$^1$ and R$^2$ have the meanings given above,
in the presence or absence of a reaction auxiliary and in the presence or absence of a diluent,
or if (b) for the preparation of compounds of the formulae (IA) and/or (IB) in which R$^5$ represents, in each case optionally substituted, alky, alkenyl or alkinyl and Q$^1$, Q$^2$, R$^1$, R$^2$, R$^3$ and R$^4$ have the meanings given above,
N-cyanoaryl nitrogen heterocycles of the general formula (IA) or (IB)
in which R$^5$ represents hydrogen and Q$^1$, Q$^2$, R$^1$, R$^2$, R$^3$ and R$^4$ have the meanings given above, are reacted with alkylating agents of the general formula (IV) or (V)

in which $R^5$ represents, in each case optionally substituted, alkyl, alkenyl or alkinyl, in the presence or absence of an acid acceptor and in the presence or absence of a diluent, or if (c) for the preparation of compounds of the formula (I) in which $R^2$ represents amino or the grouping —N($A^1$)SO$_2$A and A, $A^1$, $Q^1$, $Q^2$, $R^1$, $R^3$, $R^4$ and Z have the meanings given above, N-cyanoaryl nitrogen heterocycles of the general formula (I), in which $R^2$ represents halogen and $Q^1$, $Q^2$, $R^1$, $R^3$, $R^4$ and Z have the meanings given above, are reacted with ammonia or with amides of the general formula (VI)

$$HN(A^1)SO_2A \qquad (VI)$$

in which

A and $A^1$ have the meanings given above, in the presence or absence of an acid acceptor and in the presence or absence of a diluent.

The compounds of the formula (I) can, by analogy with process (a), also be obtained by reaction of aminoalkenoic (thio)esters of the formula (II)—above—with cyanoaryl (thio)urethanes of the formula (IIIa)

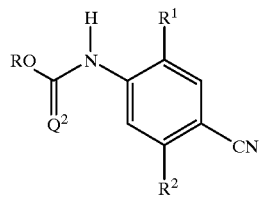

in which $Q^2$, $R^1$ and $R^2$ have the meanings given above and

R represents alkyl (in particular methyl) or aryl (in particular phenyl).

The novel N-cyanoaryl nitrogen heterocycles having sulphur-containing groupings of the general formula (I) are distinguished by high herbicidal efficiency.

In the definitions, the saturated or unsaturated hydrocarbon chains, such as alkyl, alkanediyl, alkenyl or alkinyl, are each straight-chain or branched.

Halogen generally represents fluorine, chlorine, bromine or iodine, preferably fluorine, chlorine or bromine, in particular fluorine or chlorine.

The invention preferably relates to compounds of the formula (I) in which $Q^1$ represents oxygen or sulphur, $R^1$ represents hydrogen, fluorine, chlorine or bromine, $R^2$ represents fluorine, chlorine, bromine, cyano, nitro, amino or the grouping —N($A^1$)SO$_2$A, in which A represents a radical selected from the group consisting of alkyl, alkenyl, alkinyl or dialkylamino each having up to 10 carbon atoms and each of which is optionally substituted by fluorine, chlorine, bromine, cyano or $C_1$–$C_4$-alkoxy, A further represents cycloalkyl or cycloalkylalkyl, each of which is optionally substituted by fluorine, chlorine, bromine, cyano or $C_1$–$C_4$-alkyl, having 3 to 8 carbon atoms in the cycloalkyl moiety and, if appropriate, 1 to 4 carbon atoms in the alkyl moiety, A further represents aryl or arylalkyl, each of which is optionally substituted by fluorine, chlorine, bromine, cyano, nitro, carboxy, carbamoyl, by $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl (which are each optionally substituted by fluorine and/or chlorine), by dimethylaminosulphonyl or diethylaminosulphonyl, by $C_1$–$C_4$-alkoxy-carbonyl (which is optionally substituted by fluorine, chlorine, bromine, methoxy or ethoxy), by phenyl or phenyloxy (which are each optionally substituted by fluorine, chlorine, bromine, cyano, methyl, methoxy, trifluoromethyl and/or trifluoromethoxy), having 6 or 10 carbon atoms in the aryl moiety and, if appropriate, 1 to 4 carbon atoms in the alkyl moiety, and $A^1$ represents hydrogen or formyl, or $C_1$–$C_4$-alkyl which is optionally substituted by fluorine and/or chlorine, cyano or $C_1$–$C_4$-alkoxy-carbonyl, or $C_1$–$C_4$-alkyl-carbonyl or $C_1$–$C_4$-alkoxy-carbonyl, each of which is optionally substituted by fluorine, chlorine or $C_1$–$C_4$-alkoxy, or $C_1$–$C_4$-alkylsulphonyl which is optionally substituted by fluorine and/or chlorine, or together with A represents alkanediyl having 2 to 8 carbon atoms, $R^3$ represents hydrogen, fluorine, chlorine, bromine, cyano or alkyl, which is optionally substituted by fluorine and/or chlorine, having 1 to 4 carbon atoms, $R^4$ represents alkyl, which is optionally substituted by fluorine, chlorine, bromine, methoxy or ethoxy, having 1 to 6 carbon atoms, or together with $R^3$ represents alkanediyl having 2 to 8 carbon atoms, and Z represents one of the groupings below

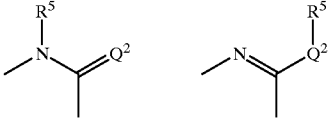

in which $Q^2$ represents oxygen or sulphur and $R^5$ represents hydrogen or alkyl, alkenyl, alkinyl or alkylcarbonyl, each of which is optionally substituted by fluorine, chlorine, bromine, cyano, $C_1$–$C_4$-alkoxy, $C_1$–$C_4$-alkyl-carbonyl or $C_1$–$C_4$-alkoxy-carbonyl, and each of which has up to 6 carbon atoms, with the proviso that at least one of the groupings $Q^1$ or $Q^2$ represents sulphur.

The invention further preferably relates to sodium salts, potassium salts, calcium salts, ammonium salts, $C_1$–$C_4$-alkyl-ammonium salts, di-($C_1$–$C_4$-alkyl)-ammonium salts, tri-($C_1$–$C_4$-alkyl)-ammonium salts, cyclopentyl- or cyclohexyl-ammonium salts and di-($C_1$–$C_4$-alkyl)-ammonium salts of compounds of the formula (I) in which $Q^1$, $R^1$, $R^2$, $R^3$, $R^4$ and Z have the meaning given above as preferred.

The invention relates in particular to compounds of the formula (I) in which $Q^1$ represents oxygen or sulphur, $R^1$ represents hydrogen, fluorine or chlorine, $R^2$ represents fluorine, chlorine, bromine, cyano, amino or the grouping —N(A$^1$)SO$_2$A, in which A represents a radical selected from the group consisting of methyl, ethyl, n- or i-propyl, n-, i-, s- or t-butyl, ethenyl, propenyl, butenyl, each of which is optionally substituted by fluorine or chlorine, or represents dimethylamino, A further represents cyclopropyl, cyclopentyl, cyclohexyl, cyclopropylmethyl, cyclopentylmethyl or cyclohexylmethyl, each of which is optionally substituted by fluorine, chlorine, bromine, methyl and/or ethyl, A further represents phenyl, naphthyl, phenylmethyl or phenylethyl, each of which is optionally substituted by fluorine, chlorine, bromine, cyano, nitro, carboxy, methyl, trifluoromethyl, methoxy, ethoxy, difluoromethoxy, trifluoromethoxy, methylthio, ethylthio, methylsulphinyl, ethylsulphinyl, methylsulphonyl, ethylsulphonyl, dimethylaminosulphonyl, methoxycarbonyl, ethoxycarbonyl, propoxycarbonyl or phenyl, and $A^1$ represents hydrogen, formyl, methyl, ethyl, acetyl, propionyl, methoxycarbonyl, ethoxycarbonyl, methylsulphonyl or ethylsulphonyl, or together with A represents trimethylene or tetramethylene, $R^3$ represents hydrogen, fluorine, chlorine, bromine, methyl, trifluoromethyl, ethyl, n- or i-propyl, $R^4$ represents methyl, ethyl, n- or i-propyl, each of which is optionally substituted by fluorine or chlorine, or together with $R^3$ represents trimethylene or tetramethylene, and Z represents one of the groupings below

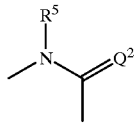 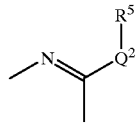

in which $Q^2$ represents oxygen or sulphur and $R^5$ represents hydrogen, methyl, difluoromethyl, cyanomethyl, ethyl, fluoroethyl, chloroethyl, difluoroethyl, dichloroethyl, trifluoroethyl, chlorodifluoroethyl, cyanoethyl, n- or i-propyl, fluoropropyl, chloropropyl, cyanopropyl, allyl, chloroallyl, propargyl, acetyl, propionyl, fluoroacetyl, chloroacetyl, difluoroacetyl, dichloroacetyl, trifluoroacetyl or trichloroacetyl, with the proviso that at least one of the groupings $Q^1$ or $Q^2$ represents sulphur.

A very particularly preferred group of compounds of the formula (I) are the compounds of the formula (IA) in which $Q^1$ represents oxygen, $Q^2$ represents sulphur, and $R^1$, $R^2$, $R^3$, $R^4$ and $R^5$ have the meaning given above as preferred in particular.

A further very particularly preferred group of compounds of the formula (I) are the compounds of the formula (IB) in which $Q^1$ represents oxygen, $Q^2$ represents sulphur, and $R^1$, $R^2$, $R^3$, $R^4$ and $R^4$ have the meaning given above as preferred in particular.

The general radical definitions or the radical definitions given in preferred areas listed above apply not only to the end products of the formula (I) but also correspondingly to each of the starting materials or intermediates necessary for preparation. These radical definitions can be combined in any manner with one another, that is also between the given ranges of preferred compounds.

Examples of the compounds of the invention of the formula (IA)—where in each case $Q^1$ represents oxygen and $Q^2$ represents sulphur—are listed in Table 1 below.

TABLE 1

Examples of the compounds of the formula (IA)

| $R^1$ | $R^2$ | $R^3$ | $R^4$ | $R^5$ |
|---|---|---|---|---|
| F | F | H | CH$_3$ | H |
| F | F | H | CH$_3$ | CH$_3$ |
| F | F | H | CH$_3$ | CHF$_2$ |
| F | NHSO$_2$C$_2$H$_5$ | H | CH$_3$ | CH$_3$ |
| F | NHSO$_2$CH$_3$ | H | CH$_3$ | CHF$_2$ |
| F | F | H | CF$_3$ | CH$_3$ |
| F | F | H | CF$_3$ | C$_3$H$_7$ |
| Cl | F | CH$_3$ | CF$_3$ | CHF$_2$ |
| F | NHSO$_2$CH$_3$ | H | CF$_3$ | CH$_3$ |
| F | NHSO$_2$C$_2$H$_5$ | H | CF$_3$ | CH$_3$ |
| F | NHSO$_2$CH$_3$ | H | CF$_3$ | CH$_2$—C≡CH |
| F | NHSO$_2$C$_2$H$_5$ | H | CF$_2$Cl | CH$_3$ |
| F | F | H | CF$_2$CF$_3$ | H |
| F | F | H | CF$_2$CF$_3$ | CH$_3$ |
| H | F | H | CF$_2$CF$_3$ | C$_2$H$_5$ |
| H | F | H | CF$_2$CF$_3$ | CH$_2$CH=CH$_2$ |
| F | NHSO$_2$CH$_3$ | H | CF$_2$CF$_3$ | CH$_3$ |
| F | NHSO$_2$C$_2$H$_5$ | H | CF$_2$CF$_3$ | CH$_3$ |
| F | F | H | CHF$_2$ | H |
| F | F | H | CHF$_2$ | CH$_3$ |
| F | F | H | CHF$_2$ | CHF$_2$ |
| F | NHSO$_2$CH$_3$ | H | CHF$_2$ | CH$_3$ |
| F | NHSO$_2$CH$_3$ | H | CHF$_2$ | CHF$_2$ |
| F | NHSO$_2$C$_2$H$_5$ | Cl | CHF$_2$ | CH$_2$CH=CH$_2$ |
| F | NHSO$_2$CF$_3$ | H | CH$_3$ | CH$_3$ |
| F | N(K)SO$_2$CH$_3$ | H | CF$_3$ | CH$_3$ |
| F | N(Na)SO$_2$CH$_3$ | H | CF$_3$ | CH$_3$ |
| F | N(K)SO$_2$C$_2$H$_5$ | H | CF$_3$ | CH$_3$ |
| F | N(Na)SO$_2$C$_2$H$_5$ | H | CF$_3$ | CH$_3$ |
| F | NHSO$_2$CH$_3$ | H | CF$_3$ | H |
| F | NSO$_2$CH$_3$<br>\|<br>CH$_3$ | H | CF$_3$ | CH$_3$ |
| F | NSO$_2$CH$_3$<br>\|<br>CO$_2$C$_2$H$_5$ | H | CF$_3$ | CH$_3$ |
| F | NSO$_2$C$_2$H$_5$<br>\|<br>CO$_2$C$_2$H$_5$ | H | CF$_3$ | CH$_3$ |
| F | NHSO$_2$C$_2$H$_5$ | H | CF$_2$CF$_3$ | CH$_3$ |
| F | F | H | CHF$_2$ | H |
| F | F | H | CHF$_2$ | CH$_3$ |
| F | F | H | CHF$_2$ | CHF$_2$ |
| F | NHSO$_2$CH$_3$ | H | CHF$_2$ | CH$_3$ |
| F | NHSO$_2$CH$_3$ | H | CHF$_2$ | CHF$_2$ |
| F | NHSO$_2$C$_2$H$_5$ | Cl | CHF$_2$ | CH$_2$CH=CH$_2$ |
| F | NHSO$_2$CF$_3$ | H | CH$_3$ | CH$_3$ |
| F | N(K)SO$_2$CH$_3$ | H | CF$_3$ | CH$_3$ |
| F | N(Na)SO$_3$CH$_3$ | H | CF$_3$ | CH$_3$ |
| F | N(K)SO$_2$C$_2$H$_5$ | H | CF$_3$ | CH$_3$ |
| F | N(Na)SO$_2$C$_2$H$_5$ | H | CF$_3$ | CH$_3$ |
| F | NHSO$_2$CH$_3$ | H | CF$_3$ | H |
| F | NSO$_2$CH$_3$<br>\|<br>CH$_3$ | H | CF$_3$ | CH$_3$ |

TABLE 1-continued

Examples of the compounds of the formula (IA)

| R¹ | R² | R³ | R⁴ | R⁵ |
|---|---|---|---|---|
| F | NSO₂CH₃ / CO₂C₂H₅ | H | CF₃ | CH₃ |
| F | NSO₂C₂H₅ / CO₂C₂H₅ | H | CF₃ | CH₃ |
| F | NSO₂C₃H₇-n / CO₂C₂H₅ | H | CF₃ | CH₃ |
| F | NSO₂C₃H₇-i / CO₂C₂H₅ | H | CF₃ | CH₃ |
| F | NSO₂CH₃ / COCH₃ | H | CF₃ | CH₃ |
| H | NHSO₂CH₃ | H | CH₃ | CH₃ |
| H | NHSO₂C₂H₅ | H | CH₃ | CH₃ |
| H | NHSO₂C₃H₇-n | H | CH₃ | CH₃ |
| H | NHSO₂C₃H₇-i | H | CH₃ | CH₃ |
| H | NHSO₂—<cyclopropyl> | H | CH₃ | CH₃ |
| H | NHSO₂C₄H₉-n | H | CH₃ | CH₃ |
| H | NHSO₂C₆H₅ | H | CH₃ | CH₃ |
| H | NHSO₂—<C₆H₄>—CH₃ | H | CH₃ | CH₃ |
| F | NHSO₂CH₃ | H | CH₃ | CH₃ |
| F | NHSO₂C₂H₅ | H | CH₃ | CH₃ |
| F | NHSO₂C₃H₇-n | H | CH₃ | CH₃ |
| F | NHSO₂C₃H₇-i | H | CH₃ | CH₃ |
| F | NHSO₂—<cyclopropyl> | H | CH₃ | CH₃ |
| F | NHSO₂C₄H₉-n | H | CH₃ | CH₃ |
| F | NHSO₂C₆H₅ | H | CH₃ | CH₃ |
| F | NHSO₂—<C₆H₄>—CH₃ | H | CH₃ | CH₃ |
| F | NHSO₂CH₃ | CH₃ | CH₃ | CH₃ |
| F | NHSO₂C₂H₅ | CH₃ | CH₃ | CH₃ |
| F | NHSO₂C₃H₇-n | CH₃ | CH₃ | CH₃ |
| F | NHSO₂C₃H₇-i | CH₃ | CH₃ | CH₃ |
| F | NHSO₂—<cyclopropyl> | CH₃ | CH₃ | CH₃ |
| F | NHSO₂C₄H₉-n | CH₃ | CH₃ | CH₃ |
| F | NHSO₂C₆H₅ | CH₃ | CH₃ | CH₃ |
| F | NHSO₂—<C₆H₄>—CH₃ | CH₃ | CH₃ | CH₃ |
| F | NHSO₂CH₃ | Cl | CH₃ | CH₃ |
| F | NHSO₂C₂H₅ | Cl | CH₃ | CH₃ |
| F | NHSO₂C₃H₇-n | Cl | CH₃ | CH₃ |
| F | NHSO₂C₃H₇-i | Cl | CH₃ | CH₃ |
| F | NHSO₂—<cyclopropyl> | Cl | CH₃ | CH₃ |
| F | NHSO₂C₄H₉-n | Cl | CH₃ | CH₃ |
| H | NHSO₂—<C₆H₄>—CH₃ | H | CH₃ | CHF₂ |
| F | NHSO₂CH₃ | H | CH₃ | CHF₂ |
| F | NHSO₂C₂H₅ | H | CH₃ | CHF₂ |
| F | NHSO₂C₃H₇-n | H | CH₃ | CHF₂ |
| F | NHSO₂C₃H₇-i | H | CH₃ | CHF₂ |
| F | NHSO₂—<cyclopropyl> | H | CH₃ | CHF₂ |
| F | NHSO₂C₄H₉-n | H | CH₃ | CHF₂ |
| F | NHSO₂C₆H₅ | H | CH₃ | CHF₂ |
| F | NHSO₂—<C₆H₄>—CH₃ | H | CH₃ | CHF₂ |
| F | NHSO₂CH₃ | CH₃ | CH₃ | CHF₂ |
| F | NHSO₂C₂H₅ | CH₃ | CH₃ | CHF₂ |
| F | NHSO₂C₃H₇-n | CH₃ | CH₃ | CHF₂ |
| F | NHSO₂C₃H₇-i | CH₃ | CH₃ | CHF₂ |
| F | NHSO₂—<cyclopropyl> | CH₃ | CH₃ | CHF₂ |
| F | NHSO₂C₄H₉-n | CH₃ | CH₃ | CHF₂ |
| F | NHSO₂C₆H₅ | CH₃ | CH₃ | CHF₂ |
| F | NHSO₂—<C₆H₄>—CH₃ | CH₃ | CH₃ | CHF₂ |
| F | NHSO₂CH₃ | Cl | CH₃ | CHF₂ |
| F | NHSO₂C₂H₅ | Cl | CH₃ | CHF₂ |
| F | NHSO₂C₃H₇-n | Cl | CH₃ | CHF₂ |
| F | NHSO₂C₃H₇-i | Cl | CH₃ | CHF₂ |
| F | NHSO₂—<cyclopropyl> | Cl | CH₃ | CHF₂ |
| F | NHSO₂C₄H₉-n | Cl | CH₃ | CHF₂ |
| F | NHSO₂C₆H₅ | Cl | CH₃ | CHF₂ |
| F | NHSO₂—<C₆H₄>—CH₃ | Cl | CH₃ | CHF₂ |
| F | NHSO₂CH₃ | F | CH₃ | CHF₂ |
| F | NHSO₂C₂H₅ | F | CH₃ | CHF₂ |
| F | NHSO₂C₃H₇-n | F | CH₃ | CHF₂ |
| F | NHSO₂C₃H₇-i | F | CH₃ | CHF₂ |

TABLE 1-continued

Examples of the compounds of the formula (IA)

| R¹ | R² | R³ | R⁴ | R⁵ |
|---|---|---|---|---|
| F | NHSO₂— | F | CH₃ | CHF₂ |
| F | NHSO₂C₄H₉-n | F | CH₃ | CHF₂ |
| F | NHSO₂C₆H₅ | F | CH₃ | CHF₂ |
| F | NHSO₂—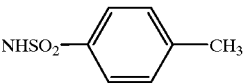—CH₃ | F | CH₃ | CHF₂ |
| F | NHSO₂CH₃ | H | CH₃ | C₂H₅ |
| F | NHSO₂C₂H₅ | H | CH₃ | C₂H₅ |
| F | NHSO₂C₃H₇-n | H | CH₃ | C₂H₅ |
| F | NHSO₂C₃H₇-i | H | CH₃ | C₂H₅ |
| F | NHSO₂— | H | CH₃ | C₂H₅ |
| F | NHSO₂C₄H₉-n | H | CH₃ | C₂H₅ |
| F | NHSO₂C₆H₅ | H | CH₃ | C₂H₅ |
| F | NHSO₂—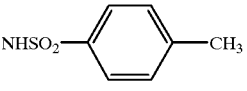—CH₃ | H | CH₃ | C₂H₅ |
| H | NHSO₂CH₃ | H | CF₃ | CH₃ |
| H | NHSO₂CF₃ | H | CF₃ | CH₃ |
| H | NHSO₂C₂H₅ | H | CF₃ | CH₃ |
| H | NHSO₂CH₂CF₃ | H | CF₃ | CH₃ |
| H | NHSO₂C₃H₇-n | H | CF₃ | CH₃ |
| H | NHSO₂C₃H₇-i | H | CF₃ | CH₃ |
| H | NHSO₂— | H | CF₃ | CH₃ |
| H | NHSO₂CH₂CH₂CH₂Cl | H | CF₃ | CH₃ |
| H | NHSO₂C₄H₉-n | H | CF₃ | CH₃ |
| H | NHSO₂C₄H₉-sec | H | CF₃ | CH₃ |
| H | NHSO₂C₄H₉-iso | H | CF₃ | CH₃ |
| H | NHSO₂C₅H₁₁-n | H | CF₃ | CH₃ |
| H | NHSO₂—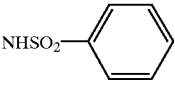 | H | CF₃ | CH₃ |
| H | NHSO₂—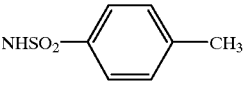—CH₃ | H | CF₃ | CH₃ |
| H | NHSO₂—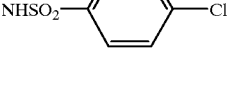—Cl | H | CF₃ | CH₃ |
| F | NHSO₂CH₃ | H | CF₃ | CH₃ |
| F | NHSO₂CF₃ | H | CF₃ | CH₃ |
| F | NHSO₂C₂H₅ | H | CF₃ | CH₃ |
| F | NHSO₂CH₂CF₃ | H | CF₃ | CH₃ |
| F | NHSO₂C₃H₇-n | H | CF₃ | CH₃ |
| F | NHSO₂C₃H₇-i | H | CF₃ | CH₃ |
| F | NHSO₂— | H | CF₃ | CH₃ |
| F | NHSO₂CH₂CH₂CH₂Cl | H | CF₃ | CH₃ |
| F | NHSO₂C₄H₉-n | H | CF₃ | CH₃ |
| F | NHSO₂C₄H₉-sec | H | CF₃ | CH₃ |
| F | NHSO₂C₄H₉-iso | H | CF₃ | CH₃ |
| F | NHSO₂C₅H₁₁-n | H | CF₃ | CH₃ |
| F | NHSO₂—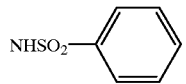 | H | CF₃ | CH₃ |
| F | NHSO₂—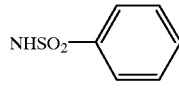—CH₃ | H | CF₃ | CH₃ |
| F | NHSO₂—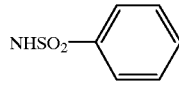—Cl | H | CF₃ | CH₃ |
| H | N(CH₃)—SO₂CH₃ | H | CF₃ | CH₃ |
| H | N(CH₃)—SO₂CF₃ | H | CF₃ | CH₃ |
| H | N(CH₃)—SO₂C₂H₅ | H | CF₃ | CH₃ |
| H | N(CH₃)—SO₂CH₂CF₃ | H | CF₃ | CH₃ |
| H | N(CH₃)—SO₂C₃H₇-n | H | CF₃ | CH₃ |
| H | N(CH₃)—SO₂C₃H₇-i | H | CF₃ | CH₃ |
| H | N(CH₃)—SO₂— | H | CF₃ | CH₃ |
| H | N(CH₃)—SO₂CH₂CH₂CH₂Cl | H | CF₃ | CH₃ |
| H | N(CH₃)—SO₂C₄H₉-n | H | CF₃ | CH₃ |
| H | N(CH₃)—SO₂C₄H₉-sec | H | CF₃ | CH₃ |
| H | N(CH₃)—SO₂C₄H₉-iso | H | CF₃ | CH₃ |

TABLE 1-continued

Examples of the compounds of the formula (IA)

| R¹ | R² | R³ | R⁴ | R⁵ |
|---|---|---|---|---|
| H | N(CH₃)—SO₂—C₆H₅ | H | CF₃ | CH₃ |
| H | N(CH₃)—SO₂—C₆H₄—CH₃ (4-) | H | CF₃ | CH₃ |
| H | N(CH₃)—SO₂—C₆H₄—Cl (4-) | H | CF₃ | CH₃ |
| F | N(CH₃)—SO₂CH₃ | H | CF₃ | CH₃ |
| F | N(CH₃)—SO₂CF₃ | H | CF₃ | CH₃ |
| F | N(CH₃)—SO₂C₂H₅ | H | CF₃ | CH₃ |
| F | N(CH₃)—SO₂CH₂CF₃ | H | CF₃ | CH₃ |
| F | N(CH₃)—SO₂C₃H₇-n | H | CF₃ | CH₃ |
| F | N(CH₃)—SO₂C₃H₇-i | H | CF₃ | CH₃ |
| F | N(CH₃)—SO₂-cyclopropyl | H | CF₃ | CH₃ |
| F | N(CH₃)—SO₂CH₂CH₂CH₂Cl | H | CF₃ | CH₃ |
| F | N(CH₃)—SO₂C₄H₉-n | H | CF₃ | CH₃ |
| F | N(CH₃)—SO₂C₄H₉-sec | H | CF₃ | CH₃ |
| F | N(CH₃)—SO₂C₄H₉-iso | H | CF₃ | CH₃ |
| F | N(CH₃)—SO₂—C₆H₅ | H | CF₃ | CH₃ |
| F | N(CH₃)—SO₂—C₆H₄—CH₃ (4-) | H | CF₃ | CH₃ |
| F | N(CH₃)—SO₂—C₆H₄—Cl (4-) | H | CF₃ | CH₃ |
| H | N(C₂H₅)—SO₂CH₃ | H | CF₃ | CH₃ |
| H | N(C₂H₅)—SO₂CF₃ | H | CF₃ | CH₃ |
| H | N(C₂H₅)—SO₂C₂H₅ | H | CF₃ | CH₃ |
| H | N(C₂H₅)—SO₂CH₂CF₃ | H | CF₃ | CH₃ |
| H | N(C₂H₅)—SO₂C₃H₇-n | H | CF₃ | CH₃ |
| H | N(C₂H₅)—SO₂C₃H₇-i | H | CF₃ | CH₃ |
| H | N(C₂H₅)—SO₂-cyclopropyl | H | CF₃ | CH₃ |
| H | N(C₂H₅)—SO₂C₄H₉-n | H | CF₃ | CH₃ |
| H | N(C₂H₅)—SO₂C₄H₉-sec | H | CF₃ | CH₃ |
| H | N(C₂H₅)—SO₂C₄H₉-iso | H | CF₃ | CH₃ |
| H | N(C₂H₅)—SO₂—C₆H₅ | H | CF₃ | CH₃ |
| H | N(C₂H₅)—SO₂—C₆H₄—CH₃ (4-) | H | CF₃ | CH₃ |

TABLE 1-continued

Examples of the compounds of the formula (IA)

| R¹ | R² | R³ | R⁴ | R⁵ |
|---|---|---|---|---|
| F | N(C₂H₅)—SO₂CH₃ | H | CF₃ | CH₃ |
| F | N(C₂H₅)—SO₂CF₃ | H | CF₃ | CH₃ |
| F | N(C₂H₅)—SO₂C₂H₅ | H | CF₃ | CH₃ |
| F | N(C₂H₅)—SO₂CH₂CF₃ | H | CF₃ | CH₃ |
| F | N(C₂H₅)—SO₂C₃H₇-n | H | CF₃ | CH₃ |
| F | N(C₂H₅)—SO₂C₃H₇-i | H | CF₃ | CH₃ |
| F | N(C₂H₅)—SO₂-cyclopropyl | H | CF₃ | CH₃ |
| F | N(C₂H₅)—SO₂C₄H₉-n | H | CF₃ | CH₃ |
| F | N(C₂H₅)—SO₂C₄H₉-sec | H | CF₃ | CH₃ |
| F | N(C₂H₅)—SO₂C₄H₉-iso | H | CF₃ | CH₃ |
| F | N(C₂H₅)—SO₂-phenyl | H | CF₃ | CH₃ |
| F | N(C₂H₅)—SO₂-(4-CH₃-phenyl) | H | CF₃ | CH₃ |
| F | N(C₂H₅)—SO₂-(4-Cl-phenyl) | H | CF₃ | CH₃ |
| F | N(C₂H₅)—SO₂CH₃ | H | CF₃ | C₂H₅ |
| F | N(C₂H₅)—SO₂CF₃ | H | CF₃ | C₂H₅ |
| F | N(C₂H₅)—SO₂C₂H₅ | H | CF₃ | C₂H₅ |
| F | N(C₂H₅)—SO₂CH₂CF₃ | H | CF₃ | C₂H₅ |
| F | N(C₂H₅)—SO₂C₃H₇-n | H | CF₃ | C₂H₅ |
| F | N(C₂H₅)—SO₂C₃H₇-i | H | CF₃ | C₂H₅ |
| F | N(C₂H₅)—SO₂-cyclopropyl | H | CF₃ | C₂H₅ |
| F | N(C₂H₅)—SO₂C₄H₉-n | H | CF₃ | C₂H₅ |
| F | N(C₂H₅)—SO₂C₄H₉-sec | H | CF₃ | C₂H₅ |
| F | N(C₂H₅)—SO₂C₄H₉-iso | H | CF₃ | C₂H₅ |
| F | N(C₂H₅)—SO₂-phenyl | H | CF₃ | C₂H₅ |
| F | N(C₂H₅)—SO₂-(4-CH₃-phenyl) | H | CF₃ | C₂H₅ |
| H | NHSO₂CH₃ | H | CF₃ | C₂H₅ |
| H | NHSO₂CF₃ | H | CF₃ | C₂H₅ |
| H | NHSO₂C₂H₅ | H | CF₃ | C₂H₅ |
| H | NHSO₂CH₂CF₃ | H | CF₃ | C₂H₅ |
| H | NHSO₂C₃H₇-n | H | CF₃ | C₂H₅ |
| H | NHSO₂C₃H₇-i | H | CF₃ | C₂H₅ |
| H | NHSO₂-cyclopropyl | H | CF₃ | C₂H₅ |
| H | NHSO₂CH₂CH₂CH₂Cl | H | CF₃ | C₂H₅ |
| H | NHSO₂C₄H₉-n | H | CF₃ | C₂H₅ |
| H | NHSO₂C₄H₉-sec | H | CF₃ | C₂H₅ |
| H | NHSO₂C₄H₉-iso | H | CF₃ | C₂H₅ |
| H | NHSO₂C₅H₁₁-n | H | CF₃ | C₂H₅ |
| H | NHSO₂-phenyl | H | CF₃ | C₂H₅ |

TABLE 1-continued

Examples of the compounds of the formula (IA)

| R¹ | R² | R³ | R⁴ | R⁵ |
|---|---|---|---|---|
| H | NHSO₂-C₆H₄-CH₃ (p-tolyl) | H | CF₃ | C₂H₅ |
| F | NHSO₂CH₃ | H | CF₃ | C₂H₅ |
| F | NHSO₂CF₃ | H | CF₃ | C₂H₅ |
| F | NHSO₂C₂H₅ | H | CF₃ | C₂H₅ |
| F | NHSO₂CH₂CF₃ | H | CF₃ | C₂H₅ |
| F | NHSO₂C₃H₇-n | H | CF₃ | C₂H₅ |
| F | NHSO₂C₃H₇-i | H | CF₃ | C₂H₅ |
| F | NHSO₂-cyclopropyl | H | CF₃ | C₂H₅ |
| F | NHSO₂CH₂CH₂CH₂Cl | H | CF₃ | C₂H₅ |
| F | NHSO₂C₄H₉-n | H | CF₃ | C₂H₅ |
| F | NHSO₂C₄H₉-sec | H | CF₃ | C₂H₅ |
| F | NHSO₂C₄H₉-iso | H | CF₃ | C₂H₅ |
| F | NHSO₂C₅H₁₁-n | H | CF₃ | C₂H₅ |
| F | NHSO₂-C₆H₅ | H | CF₃ | C₂H₅ |
| F | NHSO₂-C₆H₄-CH₃ (p-tolyl) | H | CF₃ | C₂H₅ |
| H | NHSO₂CH₃ | CH₃ | CF₃ | CH₃ |
| H | NHSO₂CF₃ | CH₃ | CF₃ | CH₃ |
| H | NHSO₂C₂H₅ | CH₃ | CF₃ | CH₃ |
| H | NHSO₂CH₂CF₃ | CH₃ | CF₃ | CH₃ |
| H | NHSO₂C₃H₇-n | CH₃ | CF₃ | CH₃ |
| H | NHSO₂C₃H₇-i | CH₃ | CF₃ | CH₃ |
| H | NHSO₂-cyclopropyl | CH₃ | CF₃ | CH₃ |
| H | NHSO₂CH₂CH₂CH₂Cl | CH₃ | CF₃ | CH₃ |
| H | NHSO₂C₄H₉-n | CH₃ | CF₃ | CH₃ |
| H | NHSO₂C₄H₉-sec | CH₃ | CF₃ | CH₃ |
| H | NHSO₂C₄H₉-iso | CH₃ | CF₃ | CH₃ |
| H | NHSO₂C₅H₁₁-n | CH₃ | CF₃ | CH₃ |
| H | NHSO₂-C₆H₅ | CH₃ | CF₃ | CH₃ |
| H | NHSO₂-C₆H₄-CH₃ (p-tolyl) | CH₃ | CF₃ | CH₃ |
| F | NHSO₂CH₃ | CH₃ | CF₃ | CH₃ |
| F | NHSO₂CF₃ | CH₃ | CF₃ | CH₃ |
| F | NHSO₂C₂H₅ | CH₃ | CF₃ | CH₃ |
| F | NHSO₂CH₂CF₃ | CH₃ | CF₃ | CH₃ |
| F | NHSO₂C₃H₇-n | CH₃ | CF₃ | CH₃ |
| F | NHSO₂C₃H₇-i | CH₃ | CF₃ | CH₃ |
| F | NHSO₂-cyclopropyl | CH₃ | CF₃ | CH₃ |
| F | NHSO₂CH₂CH₂CH₂Cl | CH₃ | CF₃ | CH₃ |
| F | NHSO₂C₄H₉-n | CH₃ | CF₃ | CH₃ |
| F | NHSO₂C₄H₉-sec | CH₃ | CF₃ | CH₃ |
| F | NHSO₂C₄H₉-iso | CH₃ | CF₃ | CH₃ |
| F | NHSO₂C₅H₁₁-n | CH₃ | CF₃ | CH₃ |
| F | NHSO₂-C₆H₅ | CH₃ | CF₃ | CH₃ |
| F | NHSO₂-C₆H₄-CH₃ (p-tolyl) | CH₃ | CF₃ | CH₃ |
| F | NHSO₂CH₃ | Cl | CF₃ | CH₃ |
| F | NHSO₂CF₃ | Cl | CF₃ | CH₃ |
| F | NHSO₂C₂H₅ | Cl | CF₃ | CH₃ |
| F | NHSO₂CH₂CF₃ | Cl | CF₃ | CH₃ |
| F | NHSO₂C₃H₇-n | Cl | CF₃ | CH₃ |
| F | NHSO₂C₃H₇-i | Cl | CF₃ | CH₃ |
| F | NHSO₂-cyclopropyl | Cl | CF₃ | CH₃ |
| F | NHSO₂CH₂CH₂CH₂Cl | Cl | CF₃ | CH₃ |
| F | NHSO₂C₄H₉-n | Cl | CF₃ | CH₃ |
| F | NHSO₂C₄H₉-sec | Cl | CF₃ | CH₃ |
| F | NHSO₂C₄H₉-iso | Cl | CF₃ | CH₃ |
| F | NHSO₂C₅H₁₁-n | Cl | CF₃ | CH₃ |
| F | NHSO₂-C₆H₅ | Cl | CF₃ | CH₃ |
| F | NHSO₂-C₆H₄-CH₃ (p-tolyl) | Cl | CF₃ | CH₃ |
| F | NHSO₂CH₃ | F | CF₃ | CH₃ |
| F | NHSO₂CF₃ | F | CF₃ | CH₃ |
| F | NHSO₂C₂H₅ | F | CF₃ | CH₃ |
| F | NHSO₂CH₂CF₃ | F | CF₃ | CH₃ |
| F | NHSO₂C₃H₇-n | F | CF₃ | CH₃ |
| F | NHSO₂C₃H₇-i | F | CF₃ | CH₃ |
| F | NHSO₂-cyclopropyl | F | CF₃ | CH₃ |
| F | NHSO₂CH₂CH₂CH₂Cl | F | CF₃ | CH₃ |
| F | NHSO₂C₄H₉-n | F | CF₃ | CH₃ |
| F | NHSO₂C₄H₉-sec | F | CF₃ | CH₃ |
| F | NHSO₂C₄H₉-iso | F | CF₃ | CH₃ |
| F | NHSO₂C₅H₁₁-n | F | CF₃ | CH₃ |
| F | NHSO₂-C₆H₅ | F | CF₃ | CH₃ |
| F | NHSO₂-C₆H₄-CH₃ (p-tolyl) | F | CF₃ | CH₃ |
| F | N(CH₃)-SO₂CH₃ | CH₃ | CF₃ | CH₃ |

TABLE 1-continued

Examples of the compounds of the formula (IA)

| R¹ | R² | R³ | R⁴ | R⁵ |
|---|---|---|---|---|
| F | N(CH₃)—SO₂CF₃ | CH₃ | CF₃ | CH₃ |
| F | N(CH₃)—SO₂C₂H₅ | CH₃ | CF₃ | CH₃ |
| F | N(CH₃)—SO₂CH₂CF₃ | CH₃ | CF₃ | CH₃ |
| F | N(CH₃)—SO₂C₃H₇-n | CH₃ | CF₃ | CH₃ |
| F | N(CH₃)—SO₂C₃H₇-i | CH₃ | CF₃ | CH₃ |
| F | N(CH₃)—SO₂-cyclopropyl | CH₃ | CF₃ | CH₃ |
| F | N(CH₃)—SO₂CH₂CH₂CH₂Cl | CH₃ | CF₃ | CH₃ |
| F | N(CH₃)—SO₂C₄H₉-n | CH₃ | CF₃ | CH₃ |
| F | N(CH₃)—SO₂C₄H₉-sec | CH₃ | CF₃ | CH₃ |
| F | N(CH₃)—SO₂C₄H₉-iso | CH₃ | CF₃ | CH₃ |
| F | N(CH₃)—SO₂-phenyl | CH₃ | CF₃ | CH₃ |
| F | N(CH₃)—SO₂-(4-CH₃-phenyl) | CH₃ | CF₃ | CH₃ |
| F | N(CH₃)—SO₂CH₃ | Cl | CF₃ | CH₃ |
| F | N(CH₃)—SO₂CF₃ | Cl | CF₃ | CH₃ |
| F | N(CH₃)—SO₂C₂H₅ | Cl | CF₃ | CH₃ |
| F | N(CH₃)—SO₂CH₂CF₃ | Cl | CF₃ | CH₃ |
| F | N(CH₃)—SO₂C₃H₇-n | Cl | CF₃ | CH₃ |
| F | N(CH₃)—SO₂C₃H₇-i | Cl | CF₃ | CH₃ |
| F | N(CH₃)—SO₂-cyclopropyl | Cl | CF₃ | CH₃ |
| F | N(CH₃)—SO₂C₄H₉-n | Cl | CF₃ | CH₃ |
| F | N(CH₃)—SO₂C₄H₉-sec | Cl | CF₃ | CH₃ |
| F | N(CH₃)—SO₂C₄H₉-iso | Cl | CF₃ | CH₃ |
| F | N(CH₃)—SO₂-phenyl | Cl | CF₃ | CH₃ |
| F | N(CH₃)—SO₂-(4-CH₃-phenyl) | Cl | CF₃ | CH₃ |
| F | N(CH₃)—SO₂CH₃ | F | CF₃ | CH₃ |
| F | N(CH₃)—SO₂CF₃ | F | CF₃ | CH₃ |
| F | N(CH₃)—SO₂C₂H₅ | F | CF₃ | CH₃ |
| F | N(CH₃)—SO₂CH₂CF₃ | F | CF₃ | CH₃ |
| F | N(CH₃)—SO₂C₃H₇-n | F | CF₃ | CH₃ |
| F | N(CH₃)—SO₂C₃H₇-i | F | CF₃ | CH₃ |

TABLE 1-continued

Examples of the compounds of the formula (IA)

| R¹ | R² | R³ | R⁴ | R⁵ |
|---|---|---|---|---|
| F | N(CH₃)—SO₂-cyclopropyl 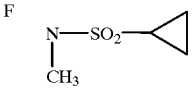 | F | CF₃ | CH₃ |
| F | N(CH₃)—SO₂CH₂CH₂CH₂Cl | F | CF₃ | CH₃ |
| F | N(CH₃)—SO₂C₄H₉-n | F | CF₃ | CH₃ |
| F | N(CH₃)—SO₂C₄H₉-sec | F | CF₃ | CH₃ |
| F | N(CH₃)—SO₂C₄H₉-iso | F | CF₃ | CH₃ |
| F | N(CH₃)—SO₂C₅H₁₀-n | F | CF₃ | CH₃ |
| F | N(CH₃)—SO₂—Ph 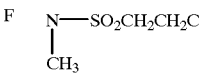 | F | CF₃ | CH₃ |
| F | N(CH₃)—SO₂—C₆H₄—CH₃ 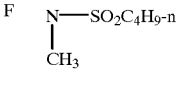 | F | CF₃ | CH₃ |
| F | NHSO₂CH₃ | H | CF₃ | CHF₂ |
| F | NHSO₂CF₃ | H | CF₃ | CHF₂ |
| F | NHSO₂C₂H₅ | H | CF₃ | CHF₂ |
| F | NHSO₂CH₂CF₃ | H | CF₃ | CHF₂ |
| F | NHSO₂C₃H₇-n | H | CF₃ | CHF₂ |
| F | NHSO₂C₃H₇-i | H | CF₃ | CHF₂ |
| F | NHSO₂-cyclopropyl 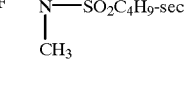 | H | CF₃ | CHF₂ |
| F | NHSO₂CH₂CH₂CH₂Cl | H | CF₃ | CHF₂ |
| F | NHSO₂C₄H₉-n | H | CF₃ | CHF₂ |
| F | NHSO₂C₄H₉-sec | H | CF₃ | CHF₂ |
| F | NHSO₂C₄H₉-iso | H | CF₃ | CHF₂ |
| F | NHSO₂C₅H₁₁-n | H | CF₃ | CHF₂ |
| F | NHSO₂—Ph 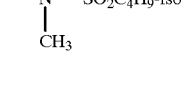 | H | CF₃ | CHF₂ |
| F | NHSO₂—C₆H₄—CH₃ 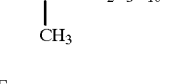 | H | CF₃ | CHF₂ |
| F | N(CH₃)—SO₂CH₃ | H | CF₃ | CHF₂ |
| F | N(CH₃)—SO₂CF₃ | H | CF₃ | CHF₂ |
| F | N(CH₃)—SO₂C₂H₅ | H | CF₃ | CHF₂ |
| F | N(CH₃)—SO₂CH₂CF₃ | H | CF₃ | CHF₂ |
| F | N(CH₃)—SO₂C₃H₇-n | H | CF₃ | CHF₂ |
| F | N(CH₃)—SO₂C₃H₇-i | H | CF₃ | CHF₂ |
| F | N(CH₃)—SO₂-cyclopropyl 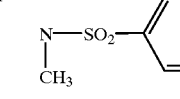 | H | CF₃ | CHF₂ |
| F | N(CH₃)—SO₂CH₂CH₂CH₂Cl | H | CF₃ | CHF₂ |
| F | N(CH₃)—SO₂C₄H₉-n | H | CF₃ | CHF₂ |
| F | N(CH₃)—SO₂C₄H₉-sec | H | CF₃ | CHF₂ |
| F | N(CH₃)—SO₂C₄H₉-iso | H | CF₃ | CHF₂ |
| F | N(CH₃)—SO₂—Ph 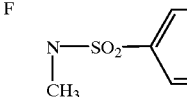 | H | CF₃ | CHF₂ |
| F | N(CH₃)—SO₂—C₆H₄—CH₃ 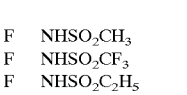 | H | CF₃ | CHF₂ |
| F | NHSO₂CH₃ | CH₃ | CF₃ | CHF₂ |
| F | NHSO₂CF₃ | CH₃ | CF₃ | CHF₂ |
| F | NHSO₂C₂H₅ | CH₃ | CF₃ | CHF₂ |
| F | NHSO₂CH₂CF₃ | CH₃ | CF₃ | CHF₂ |
| F | NHSO₂C₃H₇-n | CH₃ | CF₃ | CHF₂ |
| F | NHSO₂C₃H₇-i | CH₃ | CF₃ | CHF₂ |
| F | NHSO₂-cyclopropyl 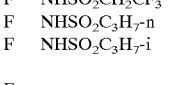 | CH₃ | CF₃ | CHF₂ |
| F | NHSO₂CH₂CH₂CH₂Cl | CH₃ | CF₃ | CHF₂ |
| F | NHSO₂C₄H₉-n | CH₃ | CF₃ | CHF₂ |
| F | NHSO₂C₄H₉-sec | CH₃ | CF₃ | CHF₂ |
| F | NHSO₂C₄H₉-iso | CH₃ | CF₃ | CHF₂ |
| F | NHSO₂C₅H₁₁-n | CH₃ | CF₃ | CHF₂ |

TABLE 1-continued

Examples of the compounds of the formula (IA)

| $R^1$ | $R^2$ | $R^3$ | $R^4$ | $R^5$ |
|---|---|---|---|---|
| F | NHSO$_2$–C$_6$H$_5$ | CH$_3$ | CF$_3$ | CHF$_2$ |
| F | NHSO$_2$–C$_6$H$_4$–CH$_3$ | CH$_3$ | CF$_3$ | CHF$_2$ |
| H | NHSO$_2$CH$_3$ | H | CHF$_2$ | CH$_3$ |
| H | NHSO$_2$CF$_3$ | H | CHF$_2$ | CH$_3$ |
| H | NHSO$_2$C$_2$H$_5$ | H | CHF$_2$ | CH$_3$ |
| H | NHSO$_2$CH$_2$CF$_3$ | H | CHF$_2$ | CH$_3$ |
| H | NHSO$_2$C$_3$H$_7$-n | H | CHF$_2$ | CH$_3$ |
| H | NHSO$_2$C$_3$H$_7$-i | H | CHF$_2$ | CH$_3$ |
| H | NHSO$_2$–cyclopropyl | H | CHF$_2$ | CH$_3$ |
| H | NHSO$_2$CH$_2$CH$_2$CH$_2$Cl | H | CHF$_2$ | CH$_3$ |
| H | NHSO$_2$C$_4$H$_9$-n | H | CHF$_2$ | CH$_3$ |
| H | NHSO$_2$C$_4$H$_9$-sec | H | CHF$_2$ | CH$_3$ |
| H | NHSO$_2$C$_4$H$_9$-iso | H | CHF$_2$ | CH$_3$ |
| H | NHSO$_2$C$_5$H$_{11}$-n | H | CHF$_2$ | CH$_3$ |
| H | NHSO$_2$–C$_6$H$_5$ | H | CHF$_2$ | CH$_3$ |
| H | NHSO$_2$–C$_6$H$_4$–CH$_3$ | H | CHF$_2$ | CH$_3$ |
| F | NHSO$_2$CH$_3$ | H | CHF$_2$ | CH$_3$ |
| F | NHSO$_2$CF$_3$ | H | CHF$_2$ | CH$_3$ |
| F | NHSO$_2$C$_2$H$_5$ | H | CHF$_2$ | CH$_3$ |
| F | NHSO$_2$CH$_2$CF$_3$ | H | CHF$_2$ | CH$_3$ |
| F | NHSO$_2$C$_3$H$_7$-n | H | CHF$_2$ | CH$_3$ |
| F | NHSO$_2$C$_3$H$_7$-i | H | CHF$_2$ | CH$_3$ |
| F | NHSO$_2$–cyclopropyl | H | CHF$_2$ | CH$_3$ |
| F | NHSO$_2$CH$_2$CH$_2$CH$_2$Cl | H | CHF$_2$ | CH$_3$ |
| F | NHSO$_2$C$_4$H$_9$-n | H | CHF$_2$ | CH$_3$ |
| F | NHSO$_2$C$_4$H$_9$-sec | H | CHF$_2$ | CH$_3$ |
| F | NHSO$_2$C$_4$H$_9$-iso | H | CHF$_2$ | CH$_3$ |
| F | NHSO$_2$C$_5$H$_{11}$-n | H | CHF$_2$ | CH$_3$ |
| F | NHSO$_2$–C$_6$H$_5$ | H | CHF$_2$ | CH$_3$ |
| F | NHSO$_2$–C$_6$H$_4$–CH$_3$ | H | CHF$_2$ | CH$_3$ |
| H | N(CH$_3$)–SO$_2$CH$_3$ | H | CHF$_2$ | CH$_3$ |
| H | N(CH$_3$)–SO$_2$CF$_3$ | H | CHF$_2$ | CH$_3$ |
| H | N(CH$_3$)–SO$_2$C$_2$H$_5$ | H | CHF$_2$ | CH$_3$ |
| H | N(CH$_3$)–SO$_2$CH$_2$CF$_3$ | H | CHF$_2$ | CH$_3$ |
| H | N(CH$_3$)–SO$_2$C$_3$H$_7$-n | H | CHF$_2$ | CH$_3$ |
| H | N(CH$_3$)–SO$_2$C$_3$H$_7$-i | H | CHF$_2$ | CH$_3$ |
| H | N(CH$_3$)–SO$_2$–cyclopropyl | H | CHF$_2$ | CH$_3$ |
| H | N(CH$_3$)–SO$_2$C$_4$H$_9$-n | H | CHF$_2$ | CH$_3$ |
| H | N(CH$_3$)–SO$_2$C$_4$H$_9$-sec | H | CHF$_2$ | CH$_3$ |
| H | N(CH$_3$)–SO$_2$C$_4$H$_9$-iso | H | CHF$_2$ | CH$_3$ |
| H | N(CH$_3$)–SO$_2$–C$_6$H$_5$ | H | CHF$_2$ | CH$_3$ |
| H | N(CH$_3$)–SO$_2$–C$_6$H$_4$–CH$_3$ | H | CHF$_2$ | CH$_3$ |
| F | N(CH$_3$)–SO$_2$CH$_3$ | H | CHF$_2$ | CH$_3$ |
| F | N(CH$_3$)–SO$_2$CF$_3$ | H | CHF$_2$ | CH$_3$ |
| F | N(CH$_3$)–SO$_2$C$_2$H$_5$ | H | CHF$_2$ | CH$_3$ |
| F | N(CH$_3$)–SO$_2$CH$_2$CF$_3$ | H | CHF$_2$ | CH$_3$ |

TABLE 1-continued

Examples of the compounds of the formula (IA)

| $R^1$ | $R^2$ | $R^3$ | $R^4$ | $R^5$ |
|---|---|---|---|---|
| F | N(CH₃)—SO₂C₃H₇-n | H | CHF₂ | CH₃ |
| F | N(CH₃)—SO₂C₃H₇-i | H | CHF₂ | CH₃ |
| F | N(CH₃)—SO₂-cyclopropyl | H | CHF₂ | CH₃ |
| F | N(CH₃)—SO₂CH₂CH₂CH₂Cl | H | CHF₂ | CH₃ |
| F | N(CH₃)—SO₂C₄H₉-n | H | CHF₂ | CH₃ |
| F | N(CH₃)—SO₂C₄H₉-sec | H | CHF₂ | CH₃ |
| F | N(CH₃)—SO₂C₄H₉-iso | H | CHF₂ | CH₃ |
| F | N(CH₃)—SO₂-phenyl | H | CHF₂ | CH₃ |
| F | N(CH₃)—SO₂-C₆H₄-CH₃ | H | CHF₂ | CH₃ |
| H | N(C₂H₅)—SO₂CH₃ | H | CHF₂ | CH₃ |
| H | N(C₂H₅)—SO₂CF₃ | H | CHF₂ | CH₃ |
| H | N(C₂H₅)—SO₂C₂H₅ | H | CHF₂ | CH₃ |
| H | N(C₂H₅)—SO₂CH₂CF₃ | H | CHF₂ | CH₃ |
| H | N(C₂H₅)—SO₂C₃H₇-n | H | CHF₂ | CH₃ |
| H | N(C₂H₅)—SO₂C₃H₇-i | H | CHF₂ | CH₃ |
| H | N(C₂H₅)—SO₂-cyclopropyl | H | CHF₂ | CH₃ |
| H | N(C₂H₅)—SO₂C₄H₉-n | H | CHF₂ | CH₃ |
| H | N(C₂H₅)—SO₂C₄H₉-sec | H | CHF₂ | CH₁₃ |
| H | N(C₂H₅)—SO₂C₄H₉-iso | H | CHF₂ | CH₃ |
| H | N(C₂H₅)—SO₂-phenyl | H | CHF₂ | CH₃ |
| H | N(C₂H₅)—SO₂-C₆H₄-CH₃ | H | CHF₂ | CH₃ |
| F | N(C₂H₅)—SO₂CH₃ | H | CHF₂ | CH₃ |
| F | N(C₂H₅)—SO₂CF₃ | H | CHF₂ | CH₃ |
| F | N(C₂H₅)—SO₂C₂H₅ | H | CHF₂ | CH₃ |
| F | N(C₂H₅)—SO₂CH₂CF₃ | H | CHF₂ | CH₃ |
| F | N(C₂H₅)—SO₂C₃H₇-n | H | CHF₂ | CH₃ |
| F | N(C₂H₅)—SO₂C₃H₇-i | H | CHF₂ | CH₃ |
| F | N(C₂H₅)—SO₂-cyclopropyl | H | CHF₂ | CH₃ |
| F | N(C₂H₅)—SO₂CH₂CH₂CH₂Cl | H | CHF₂ | CH₃ |
| F | N(C₂H₅)—SO₂C₄H₉-n | H | CHF₂ | CH₃ |

TABLE 1-continued

Examples of the compounds of the formula (IA)

| R¹ | R² | R³ | R⁴ | R⁵ |
|---|---|---|---|---|
| F | N(C₂H₅)—SO₂C₄H₉-sec | H | CHF₂ | CH₃ |
| F | N(C₂H₅)—SO₂C₄H₉-iso | H | CHF₂ | CH₃ |
| F | N(C₂H₅)—SO₂—C₆H₅ | H | CHF₂ | CH₃ |
| F | N(C₂H₅)—SO₂—C₆H₄—CH₃ (4-) | H | CHF₂ | CH₃ |
| F | N(C₂H₅)—SO₂CH₃ | H | CHF₂ | C₂H₅ |
| F | N(C₂H₅)—SO₂CF₃ | H | CHF₂ | C₂H₅ |
| F | N(C₂H₅)—SO₂C₂H₅ | H | CHF₂ | C₂H₅ |
| F | N(C₂H₅)—SO₂CH₂CF₃ | H | CHF₂ | C₂H₅ |
| F | N(C₂H₅)—SO₂C₃H₇-n | H | CHF₂ | C₂H₅ |
| F | N(C₂H₅)—SO₂C₃H₇-i | H | CHF₂ | C₂H₅ |
| F | N(C₂H₅)—SO₂-cyclopropyl | H | CHF₂ | C₂H₅ |
| F | N(C₂H₅)—SO₂C₄H₉-n | H | CHF₂ | C₂H₅ |
| F | N(C₂H₅)—SO₂C₄H₉-sec | H | CHF₂ | C₂H₅ |
| F | N(C₂H₅)—SO₂C₄H₉-iso | H | CHF₂ | C₂H₅ |
| F | N(C₂H₅)—SO₂—C₆H₅ | H | CHF₂ | C₂H₅ |
| F | N(C₂H₅)—SO₂—C₆H₄—CH₃ (4-) | H | CHF₂ | C₂H₅ |
| H | NHSO₂CH₃ | H | CHF₂ | C₂H₅ |
| H | NHSO₂CF₃ | H | CHF₂ | C₂H₅ |
| H | NHSO₂C₂H₅ | H | CHF₂ | C₂H₅ |
| H | NHSO₂CH₂CF₃ | H | CHF₂ | C₂H₅ |
| H | NHSO₂C₃H₇-n | H | CHF₂ | C₂H₅ |
| H | NHSO₂C₃H₇-i | H | CHF₂ | C₂H₅ |
| H | NHSO₂-cyclopropyl | H | CHF₂ | C₂H₅ |
| H | NHSO₂CH₂CH₂CH₂Cl | H | CHF₂ | C₂H₅ |
| H | NHSO₂C₄H₉-n | H | CHF₂ | C₂H₅ |
| H | NHSO₂C₄H₉-sec | H | CHF₂ | C₂H₅ |
| H | NHSO₂C₄H₉-iso | H | CHF₂ | C₂H₅ |
| H | NHSO₂C₅H₁₀-n | H | CHF₂ | C₂H₅ |
| H | NHSO₂—C₆H₅ | H | CHF₂ | C₂H₅ |
| H | NHSO₂—C₆H₄—CH₃ (4-) | H | CHF₂ | C₂H₅ |
| F | NHSO₂CH₃ | H | CHF₂ | C₂H₅ |
| F | NHSO₂CF₃ | H | CHF₂ | C₂H₅ |
| F | NHSO₂C₂H₅ | H | CHF₂ | C₂H₅ |
| F | NHSO₂CH₂CF₃ | R | CHF₂ | C₂H₅ |
| F | NHSO₂C₃H₇-n | H | CHF₂ | C₂H₅ |
| F | NHSO₂C₃H₇-i | H | CHF₂ | C₂H₅ |
| F | NHSO₂-cyclopropyl | H | CHF₂ | C₂H₅ |
| F | NHSO₂CH₂CH₂CH₂Cl | H | CHF₂ | C₂H₅ |
| F | NHSO₂C₄H₉-n | H | CHF₂ | C₂H₅ |
| F | NHSO₂C₄H₉-sec | H | CHF₂ | C₂H₅ |
| F | NHSO₂C₄H₉-iso | H | CHF₂ | C₂H₅ |
| F | NHSO₂C₅H₁₁-n | H | CHF₂ | C₂H₅ |
| F | NHSO₂—C₆H₅ | H | CHF₂ | C₂H₅ |
| F | NHSO₂—C₆H₄—CH₃ (4-) | H | CHF₂ | C₂H₅ |
| H | NHSO₂CH₃ | CH₃ | CHF₂ | CH₃ |
| H | NHSO₂CF₃ | CH₃ | CHF₂ | CH₃ |
| H | NHSO₂C₂H₅ | CH₃ | CHF₂ | CH₃ |
| H | NHSO₂CH₂CF₃ | CH₃ | CHF₂ | CH₃ |
| H | NHSO₂C₃H₇-n | CH₃ | CHF₂ | CH₃ |
| H | NHSO₂C₃H₇-i | CH₃ | CHF₂ | CH₃ |
| H | NHSO₂-cyclopropyl | CH₃ | CHF₂ | CH₃ |
| H | NHSO₂CH₂CH₂CH₂Cl | CH₃ | CHF₂ | CH₃ |
| H | NHSO₂C₄H₉-n | CH₃ | CHF₂ | CH₃ |

TABLE 1-continued

Examples of the compounds of the formula (IA)

| R¹ | R² | R³ | R⁴ | R⁵ |
|---|---|---|---|---|
| H | NHSO₂C₄H₉-sec | CH₃ | CHF₂ | CH₃ |
| H | NHSO₂C₄H₉-iso | CH₃ | CHF₂ | CH₃ |
| H | NHSO₂C₅H₁₁-n | CH₃ | CHF₂ | CH₃ |
| H | 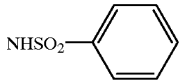 | CH₃ | CHF₂ | CH₃ |
| H | 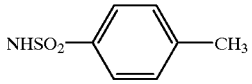 | CH₃ | CHF₂ | CH₃ |
| F | NHSO₂CH₃ | CH₃ | CHF₂ | CH₃ |
| F | NHSO₂CF₃ | CH₃ | CHF₂ | CH₃ |
| F | NHSO₂C₂H₅ | CH₃ | CHF₂ | CH₃ |
| F | NHSO₂CH₂CF₃ | CH₃ | CHF₂ | CH₃ |
| F | NHSO₂C₃H₇-n | CH₃ | CHF₂ | CH₃ |
| F | NHSO₂C₃H₇-i | CH₃ | CHF₂ | CH₃ |
| F | 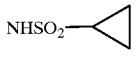 | CH₃ | CHF₂ | CH₃ |
| F | NHSO₂CH₂CH₂CH₂Cl | CH₃ | CHF₂ | CH₃ |
| F | NHSO₂C₄H₉-n | CH₃ | CHF₂ | CH₃ |
| F | NHSO₂C₄H₉-sec | CH₃ | CHF₂ | CH₃ |
| F | NHSO₂C₄H₉-iso | CH₃ | CHF₂ | CH₃ |
| F | NHSO₂C₅H₁₁-n | CH₃ | CHF₂ | CH₃ |
| F | 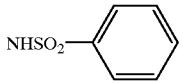 | CH₃ | CHF₂ | CH₃ |
| F | 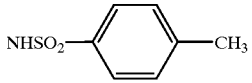 | CH₃ | CHF₂ | CH₃ |
| F | NHSO₂CH₃ | Cl | CHF₂ | CH₃ |
| F | NHSO₂CF₃ | Cl | CHF₂ | CH₃ |
| F | NHSO₂C₂H₅ | Cl | CHF₂ | CH₃ |
| F | NHSO₂CH₂CF₃ | Cl | CHF₂ | CH₃ |
| F | NHSO₂C₃H₇-n | Cl | CHF₂ | CH₃ |
| F | NHSO₂C₃H₇-i | Cl | CHF₂ | CH₃ |
| F | 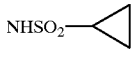 | Cl | CHF₂ | CH₃ |
| F | NHSO₂CH₂CH₂CH₂Cl | Cl | CHF₂ | CH₃ |
| F | NHSO₂C₄H₉-n | Cl | CHF₂ | CH₃ |
| F | NHSO₂C₄H₉-sec | Cl | CHF₂ | CH₃ |
| F | NHSO₂C₄H₉-iso | Cl | CHF₂ | CH₃ |
| F | NHSO₂C₅H₁₁-n | Cl | CHF₂ | CH₃ |
| F | 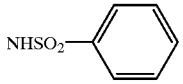 | Cl | CHF₂ | CH₃ |
| F | 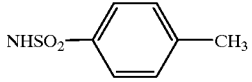 | Cl | CHF₂ | CH₃ |
| F | NHSO₂CH₃ | F | CHF₂ | CH₃ |
| F | NHSO₂CF₃ | F | CHF₂ | CH₃ |
| F | NHSO₂C₂H₅ | F | CHF₂ | CH₃ |
| F | NHSO₂CH₂CF₃ | F | CHF₂ | CH₃ |
| F | NHSO₂C₃H₇-n | F | CHF₂ | CH₃ |
| F | NHSO₂C₃H₇-i | F | CHF₂ | CH₃ |
| F | 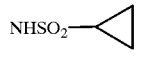 | F | CHF₂ | CH₃ |
| F | NHSO₂CH₂CH₂CH₂Cl | F | CHF₂ | CH₃ |
| F | NHSO₂C₄H₉-n | F | CHF₂ | CH₃ |
| F | NHSO₂C₄H₉-sec | F | CHF₂ | CH₃ |
| F | NHSO₂C₄H₉-iso | F | CHF₂ | CH₃ |
| F | NHSO₂C₅H₁₁-n | F | CHF₂ | CH₃ |
| F | 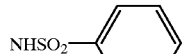 | F | CHF₂ | CH₃ |
| F |  | F | CHF₂ | CH₃ |
| F |  | CH₃ | CHF₂ | CH₃ |
| F |  | CH₃ | CHF₂ | CH₃ |
| F |  | CH₃ | CHF₂ | CH₃ |
| F |  | CH₃ | CHF₂ | CH₃ |
| F |  | CH₃ | CHF₂ | CH₃ |
| F |  | CH₃ | CHF₂ | CH₃ |
| F |  | CH₃ | CHF₂ | CH₃ |
| F |  | CH₃ | CHF₂ | CH₃ |
| F |  | CH₃ | CHF₂ | CH₃ |
| F |  | CH₃ | CHF₂ | CH₃ |

TABLE 1-continued

Examples of the compounds of the formula (IA)

| R¹ | R² | R³ | R⁴ | R⁵ |
|---|---|---|---|---|
| F | N(CH₃)—SO₂—C₆H₅ | CH₃ | CHF₂ | CH₃ |
| F | N(CH₃)—SO₂—C₆H₄—CH₃ (p) | CH₃ | CHF₂ | CH₃ |
| F | N(CH₃)—SO₂CH₃ | Cl | CHF₂ | CH₃ |
| F | N(CH₃)—SO₂CF₃ | Cl | CHF₂ | CH₃ |
| F | N(CH₃)—SO₂C₂H₅ | Cl | CHF₂ | CH₃ |
| F | N(CH₃)—SO₂CH₂CF₃ | Cl | CHF₂ | CH₃ |
| F | N(CH₃)—SO₂C₃H₇-n | Cl | CHF₂ | CH₃ |
| F | N(CH₃)—SO₂C₃H₇-i | Cl | CHF₂ | CH₃ |
| F | N(CH₃)—SO₂-cyclopropyl | Cl | CHF₂ | CH₃ |
| F | N(CH₃)—SO₂C₄H₉-n | Cl | CHF₂ | CH₃ |
| F | N(CH₃)—SO₂C₄H₉-sec | Cl | CHF₂ | CH₃ |
| F | N(CH₃)—SO₂C₄H₉-iso | Cl | CHF₂ | CH₃ |
| F | N(CH₃)—SO₂—C₆H₅ | Cl | CHF₂ | CH₃ |
| F | N(CH₃)—SO₂—C₆H₄—CH₃ (p) | Cl | CHF₂ | CH₃ |
| F | N(CH₃)—SO₂CH₃ | F | CHF₂ | CH₃ |
| F | N(CH₃)—SO₂CF₃ | F | CHF₂ | CH₃ |
| F | N(CH₃)—SO₂C₂H₅ | F | CHF₂ | CH₃ |
| F | N(CH₃)—SO₂CH₂CF₃ | F | CHF₂ | CH₃ |
| F | N(CH₃)—SO₂C₃H₇-n | F | CHF₂ | CH₃ |
| F | N(CH₃)—SO₂C₃H₇-i | F | CHF₂ | CH₃ |
| F | N(CH₃)—SO₂-cyclopropyl | F | CHF₂ | CH₃ |
| F | N(CH₃)—SO₂C₄H₉-n | F | CHF₂ | CH₃ |
| F | N(CH₃)—SO₂C₄H₉-sec | F | CHF₂ | CH₃ |
| F | N(CH₃)—SO₂C₄H₉-iso | F | CHF₂ | CH₃ |
| F | N(CH₃)—SO₂—C₆H₅ | F | CHF₂ | CH₃ |
| F | N(CH₃)—SO₂—C₆H₄—CH₃ (p) | F | CHF₂ | CH₃ |
| F | NHSO₂CH₃ | H | CHF₂ | CHF₂ |
| F | NHSO₂CF₃ | H | CHF₂ | CHF₂ |
| F | NHSO₂C₂H₅ | H | CHF₂ | CHF₂ |
| F | NHSO₂CH₂CF₃ | H | CHF₂ | CHF₂ |
| F | NHSO₂C₃H₇-n | H | CHF₂ | CHF₂ |
| F | NHSO₂C₃H₇-i | H | CHF₂ | CHF₂ |
| F | NHSO₂-cyclopropyl | H | CHF₂ | CHF₂ |
| F | NHSO₂CH₂CH₂CH₂Cl | H | CHF₂ | CHF₂ |
| F | NHSO₂C₄H₉-n | H | CHF₂ | CHF₂ |
| F | NHSO₂C₄H₉-sec | H | CHF₂ | CHF₂ |
| F | NHSO₂C₄H₉-iso | H | CHF₂ | CHF₂ |
| F | NHSO₂C₅H₁₁-n | H | CHF₂ | CHF₂ |

TABLE 1-continued

Examples of the compounds of the formula (IA)

| R¹ | R² | R³ | R⁴ | R⁵ |
|---|---|---|---|---|
| F | NHSO₂-C₆H₅ | H | CHF₂ | CHF₂ |
| F | NHSO₂-C₆H₄-CH₃ | H | CHF₂ | CHF₂ |
| F | N(CH₃)-SO₂CH₃ | H | CHF₂ | CHF₂ |
| F | N(CH₃)-SO₂CF₃ | H | CHF₂ | CHF₂ |
| F | N(CH₃)-SO₂C₂H₅ | H | CHF₂ | CHF₂ |
| F | N(CH₃)-SO₂CH₂CF₃ | H | CHF₂ | CHF₂ |
| F | N(CH₃)-SO₂C₃H₇-n | H | CHF₂ | CHF₂ |
| F | N(CH₃)-SO₂C₃H₇-i | H | CHF₂ | CHF₂ |
| F | N(CH₃)-SO₂-cyclopropyl | H | CHF₂ | CHF₂ |
| F | N(CH₃)-SO₂C₄H₉-n | H | CHF₂ | CHF₂ |
| F | N(CH₃)-SO₂C₄H₉-sec | H | CHF₂ | CHF₂ |
| F | N(CH₃)-SO₂C₄H₉-iso | H | CHF₂ | CHF₂ |
| F | N(CH₃)-SO₂-C₆H₅ | H | CHF₂ | CHF₂ |
| F | N(CH₃)-SO₂-C₆H₄-CH₃ | H | CHF₂ | CHF₂ |
| F | NHSO₂CH₃ | CH₃ | CHF₂ | CHF₂ |
| F | NHSO₂CF₃ | CH₃ | CHF₂ | CHF₂ |
| F | NHSO₂C₂H₅ | CH₃ | CHF₂ | CHF₂ |
| F | NHSO₂CH₂CF₃ | CH₃ | CHF₂ | CHF₂ |
| F | NHSO₂C₃H₇-n | CH₃ | CHF₂ | CHF₂ |
| F | NHSO₂C₃H₇-i | CH₃ | CHF₂ | CHF₂ |
| F | NHSO₂-cyclopropyl | CH₃ | CHF₂ | CHF₂ |
| F | NHSO₂CH₂CH₂CH₂Cl | CH₃ | CHF₂ | CHF₂ |
| F | NHSO₂C₄H₉-n | CH₃ | CHF₂ | CHF₂ |
| F | NHSO₂C₄H₉-sec | CH₃ | CHF₂ | CHF₂ |
| F | NHSO₂C₄H₉-iso | CH₃ | CHF₂ | CHF₂ |
| F | NHSO₂C₅H₁₁-n | CH₃ | CHF₂ | CHF₂ |
| F | NHSO₂-C₆H₅ | CH₃ | CHF₂ | CHF₂ |
| F | NHSO₂-C₆H₄-CH₃ | CH₃ | CHF₂ | CHF₂ |
| H | NHSO₂CH₃ | H | C₂F₅ | CH₃ |
| H | NHSO₂CF₃ | H | C₂F₅ | CH₃ |
| H | NHSO₂C₂H₅ | H | C₂F₅ | CH₃ |
| H | NHSO₂CH₂CF₃ | H | C₂F₅ | CH₃ |
| H | NHSO₂C₃H₇-n | H | C₂F₅ | CH₃ |
| H | NHSO₂C₃H₇-i | H | C₂F₅ | CH₃ |
| H | NHSO₂-cyclopropyl | H | C₂F₅ | CH₃ |
| H | NHSO₂CH₂CH₂CH₂Cl | H | C₂F₅ | CH₃ |
| H | NHSO₂C₄H₉-n | H | C₂F₅ | CH₃ |
| H | NHSO₂C₄H₉-sec | H | C₂F₅ | CH₃ |
| H | NHSO₂C₄H₉-iso | H | C₂F₅ | CH₃ |
| H | NHSO₂C₅H₁₁-n | H | C₂F₅ | CH₃ |
| H | NHSO₂-C₆H₅ | H | C₂F₅ | CH₃ |
| H | NHSO₂-C₆H₄-CH₃ | H | C₂F₅ | CH₃ |
| F | NHSO₂CH₃ | H | C₂F₅ | CH₃ |
| F | NHSO₂CF₃ | H | C₂F₅ | CH₃ |
| F | NHSO₂C₂H₅ | H | C₂F₅ | CH₃ |
| F | NHSO₂CH₂CF₃ | H | C₂F₅ | CH₃ |
| F | NHSO₂C₃H₇-n | H | C₂F₅ | CH₃ |
| F | NHSO₂C₃H₇-i | H | C₂F₅ | CH₃ |
| F | NHSO₂-cyclopropyl | H | C₂F₅ | CH₃ |
| F | NHSO₂CH₂CH₂CH₂Cl | H | C₂F₅ | CH₃ |
| F | NHSO₂C₄H₉-n | H | C₂F₅ | CH₃ |
| F | NHSO₂C₄H₉-sec | H | C₂F₅ | CH₃ |
| F | NHSO₂C₄H₉-iso | H | C₂F₅ | CH₃ |
| F | NHSO₂C₅H₁₁-n | H | C₂F₅ | CH₃ |
| F | NHSO₂-C₆H₅ | H | C₂F₅ | CH₃ |

TABLE 1-continued

Examples of the compounds of the formula (IA)

| R$^1$ | R$^2$ | R$^3$ | R$^4$ | R$^5$ |
|---|---|---|---|---|
| F | 4-CH$_3$-C$_6$H$_4$-SO$_2$NH- | H | C$_2$F$_5$ | CH$_3$ |
| H | N(CH$_3$)SO$_2$CH$_3$ | H | C$_2$F$_5$ | CH$_3$ |
| H | N(CH$_3$)SO$_2$CF$_3$ | H | C$_2$F$_5$ | CH$_3$ |
| H | N(CH$_3$)SO$_2$C$_2$H$_5$ | H | C$_2$F$_5$ | CH$_3$ |
| H | N(CH$_3$)SO$_2$CH$_2$CF$_3$ | H | C$_2$F$_5$ | CH$_3$ |
| H | N(CH$_3$)SO$_2$C$_3$H$_7$-n | H | C$_2$F$_5$ | CH$_3$ |
| H | N(CH$_3$)SO$_2$C$_3$H$_7$-i | H | C$_2$F$_5$ | CH$_3$ |
| H | N(CH$_3$)SO$_2$-cyclopropyl | H | C$_2$F$_5$ | CH$_3$ |
| H | N(CH$_3$)SO$_2$C$_4$H$_9$-n | H | C$_2$F$_5$ | CH$_3$ |
| H | N(CH$_3$)SO$_2$C$_4$H$_9$-sec | H | C$_2$F$_5$ | CH$_3$ |
| H | N(CH$_3$)SO$_2$C$_4$H$_9$-iso | H | C$_2$F$_5$ | CH$_3$ |
| H | N(CH$_3$)SO$_2$-C$_6$H$_5$ | H | C$_2$F$_5$ | CH$_3$ |
| H | N(CH$_3$)SO$_2$-4-CH$_3$-C$_6$H$_4$ | H | C$_2$F$_5$ | CH$_3$ |
| F | N(CH$_3$)SO$_2$CH$_3$ | H | C$_2$F$_5$ | CH$_3$ |
| F | N(CH$_3$)SO$_2$CF$_3$ | H | C$_2$F$_5$ | CH$_3$ |
| F | N(CH$_3$)SO$_2$C$_2$H$_5$ | H | C$_2$F$_5$ | CH$_3$ |
| F | N(CH$_3$)SO$_2$CH$_2$CF$_3$ | H | C$_2$F$_5$ | CH$_3$ |
| F | N(CH$_3$)SO$_2$C$_3$H$_7$-n | H | C$_2$F$_5$ | CH$_3$ |
| F | N(CH$_3$)SO$_2$C$_3$H$_7$-i | H | C$_2$F$_5$ | CH$_3$ |
| F | N(CH$_3$)SO$_2$-cyclopropyl | H | C$_2$F$_5$ | CH$_3$ |
| F | N(CH$_3$)SO$_2$C$_4$H$_9$-n | H | C$_2$F$_5$ | CH$_3$ |
| F | N(CH$_3$)SO$_2$C$_4$H$_9$-sec | H | C$_2$F$_5$ | CH$_3$ |
| F | N(CH$_3$)SO$_2$C$_4$H$_9$-iso | H | C$_2$F$_5$ | CH$_3$ |
| F | N(CH$_3$)SO$_2$-C$_6$H$_5$ | H | C$_2$F$_5$ | CH$_3$ |
| F | N(CH$_3$)SO$_2$-4-CH$_3$-C$_6$H$_4$ | H | C$_2$F$_5$ | CH$_3$ |
| H | N(C$_2$H$_5$)SO$_2$CH$_3$ | H | C$_2$F$_5$ | CH$_3$ |
| H | N(C$_2$H$_5$)SO$_2$CF$_3$ | H | C$_2$F$_5$ | CH$_3$ |
| H | N(C$_2$H$_5$)SO$_2$C$_2$H$_5$ | H | C$_2$F$_5$ | CH$_3$ |
| H | N(C$_2$H$_5$)SO$_2$CH$_2$CF$_3$ | H | C$_2$F$_5$ | CH$_3$ |
| H | N(C$_2$H$_5$)SO$_2$C$_3$H$_7$-n | H | C$_2$F$_5$ | CH$_3$ |

TABLE 1-continued

Examples of the compounds of the formula (IA)

| R¹ | R² | R³ | R⁴ | R⁵ |
|---|---|---|---|---|
| H | N(C₂H₅)—SO₂C₃H₇-i | H | C₂F₅ | CH₃ |
| H | N(C₂H₅)—SO₂-cyclopropyl | H | C₂F₅ | CH₃ |
| H | N(C₂H₅)—SO₂C₄H₉-n | H | C₂F₅ | CH₃ |
| H | N(C₂H₅)—SO₂C₄H₉-sec | H | C₂F₅ | CH₃ |
| H | N(C₂H₅)—SO₂C₄H₉-iso | H | C₂F₅ | CH₃ |
| H | N(C₂H₅)—SO₂-C₆H₅ | H | C₂F₅ | CH₃ |
| H | N(C₂H₅)—SO₂-C₆H₄-CH₃ | H | C₂F₅ | CH₃ |
| F | N(C₂H₅)—SO₂CH₃ | H | C₂F₅ | CH₃ |
| F | N(C₂H₅)—SO₂CF₃ | H | C₂F₅ | CH₃ |
| F | N(C₂H₅)—SO₂C₂H₅ | H | C₂F₅ | CH₃ |
| F | N(C₂H₅)—SO₂CH₂CF₃ | H | C₂F₅ | CH₃ |
| F | N(C₂H₅)—SO₂C₃H₇-n | H | C₂F₅ | CH₃ |
| F | N(C₂H₅)—SO₂C₃H₇-i | H | C₂F₅ | CH₃ |
| F | N(C₂H₅)—SO₂-cyclopropyl | H | C₂F₅ | CH₃ |
| F | N(C₂H₅)—SO₂C₄H₉-n | H | C₂F₅ | CH₃ |
| F | N(C₂H₅)—SO₂C₄H₉-sec | H | C₂F₅ | CH₃ |
| F | N(C₂H₅)—SO₂C₄H₉-iso | H | C₂F₅ | CH₃ |
| F | N(C₂H₅)—SO₂-C₆H₅ | H | C₂F₅ | CH₃ |
| F | N(C₂H₅)—SO₂-C₆H₄-CH₃ | H | C₂F₅ | CH₃ |
| F | N(C₂H₅)—SO₂CH₃ | H | C₂F₅ | C₂H₅ |
| F | N(C₂H₅)—SO₂CF₃ | H | C₂F₅ | C₂H₅ |
| F | N(C₂H₅)—SO₂C₂H₅ | H | C₂F₅ | C₂H₅ |
| F | N(C₂H₅)—SO₂CH₂CF₃ | H | C₂F₅ | C₂H₅ |
| F | N(C₂H₅)—SO₂C₃H₇-n | H | C₂F₅ | C₂H₅ |
| F | N(C₂H₅)—SO₂C₃H₇-i | H | C₂F₅ | C₂H₅ |
| F | N(C₂H₅)—SO₂-cyclopropyl | H | C₂F₅ | C₂H₅ |
| F | N(C₂H₅)—SO₂C₄H₉-n | H | C₂F₅ | C₂H₅ |
| F | N(C₂H₅)—SO₂C₄H₉-sec | H | C₂F₅ | C₂H₅ |
| F | N(C₂H₅)—SO₂C₄H₉-iso | H | C₂F₅ | C₂H₅ |
| F | N(C₂H₅)—SO₂-C₆H₅ | H | C₂F₅ | C₂H₅ |

TABLE 1-continued

Examples of the compounds of the formula (IA)

| R¹ | R² | R³ | R⁴ | R⁵ |
|---|---|---|---|---|
| F | -N(C₂H₅)-SO₂-C₆H₄-CH₃ (para) | H | C₂F₅ | C₂H₅ |
| H | NHSO₂CH₃ | H | C₂F₅ | C₂H₅ |
| H | NHSO₂CF₃ | H | C₂F₅ | C₂H₅ |
| H | NHSO₂C₂H₅ | H | C₂F₅ | C₂H₅ |
| H | NHSO₂CH₂CF₃ | H | C₂F₅ | C₂H₅ |
| H | NHSO₂C₃H₇-n | H | C₂F₅ | C₂H₅ |
| H | NHSO₂C₃H₇-i | H | C₂F₅ | C₂H₅ |
| H | NHSO₂-cyclopropyl | H | C₂F₅ | C₂H₅ |
| H | NHSO₂CH₂CH₂CH₂Cl | H | C₂F₅ | C₂H₅ |
| H | NHSO₂C₄H₉-n | H | C₂F₅ | C₂H₅ |
| H | NHSO₂C₄H₉-sec | H | C₂F₅ | C₂H₅ |
| H | NHSO₂C₄H₉-iso | H | C₂F₅ | C₂H₅ |
| H | NHSO₂C₅H₁₁-n | H | C₂F₅ | C₂H₅ |
| H | NHSO₂-C₆H₅ | H | C₂F₅ | C₂H₅ |
| H | NHSO₂-C₆H₄-CH₃ (para) | H | C₂F₅ | C₂H₅ |
| F | NHSO₂CH₃ | H | C₂F₅ | C₂H₅ |
| F | NHSO₂CF₃ | H | C₂F₅ | C₂H₅ |
| F | NHSO₂C₂H₅ | H | C₂F₅ | C₂H₅ |
| F | NHSO₂CH₂CF₃ | H | C₂F₅ | C₂H₅ |
| F | NHSO₂C₃H₇-n | H | C₂F₅ | C₂H₅ |
| F | NHSO₂C₃H₇-i | H | C₂F₅ | C₂H₅ |
| F | NHSO₂-cyclopropyl | H | C₂F₅ | C₂H₅ |
| F | NHSO₂CH₂CH₂CH₂Cl | H | C₂F₅ | C₂H₅ |
| F | NHSO₂C₄H₉-n | H | C₂F₅ | C₂H₅ |
| F | NHSO₂C₄H₉-sec | H | C₂F₅ | C₂H₅ |
| F | NHSO₂C₄H₉-iso | H | C₂F₅ | C₂H₅ |
| F | NHSO₂C₅H₁₁-n | H | C₂F₅ | C₂H₅ |
| F | NHSO₂-C₆H₅ | H | C₂F₅ | C₂H₅ |
| F | NHSO₂-C₆H₄-CH₃ (para) | H | C₂F₅ | C₂H₅ |
| H | NHSO₂CH₃ | CH₃ | C₂F₅ | CH₃ |
| H | NHSO₂CF₃ | CH₃ | C₂F₅ | CH₃ |
| H | NHSO₂C₂H₅ | CH₃ | C₂F₅ | CH₃ |
| H | NHSO₂CH₂CF₃ | CH₃ | C₂F₅ | CH₃ |
| H | NHSO₂C₃H₇-n | CH₃ | C₂F₅ | CH₃ |
| H | NHSO₂C₃H₇-i | CH₃ | C₂F₅ | CH₃ |
| H | NHSO₂-cyclopropyl | CH₃ | C₂F₅ | CH₃ |
| H | NHSO₂CH₂CH₂CH₂Cl | CH₃ | C₂F₅ | CH₃ |
| H | NHSO₂C₄H₉-n | CH₃ | C₂F₅ | CH₃ |
| H | NHSO₂C₄H₉-sec | CH₃ | C₂F₅ | CH₃ |
| H | NHSO₂C₄H₉-iso | CH₃ | C₂F₅ | CH₃ |
| H | NHSO₂C₅H₁₁-n | CH₃ | C₂F₅ | CH₃ |
| H | NHSO₂-C₆H₅ | CH₃ | C₂F₅ | CH₃ |
| H | NHSO₂-C₆H₄-CH₃ (para) | CH₃ | C₂F₅ | CH₃ |
| F | NHSO₂CH₃ | CH₃ | C₂F₅ | CH₃ |
| F | NHSO₂CF₃ | CH₃ | C₂F₅ | CH₃ |
| F | NHSO₂C₂H₅ | CH₃ | C₂F₅ | CH₃ |
| F | NHSO₂CH₂CF₃ | CH₃ | C₂F₅ | CH₃ |
| F | NHSO₂C₃H₇-n | CH₃ | C₂F₅ | CH₃ |
| F | NHSO₂C₃H₇-i | CH₃ | C₂F₅ | CH₃ |
| F | NHSO₂-cyclopropyl | CH₃ | C₂F₅ | CH₃ |
| F | NHSO₂CH₂CH₂CH₂Cl | CH₃ | C₂F₅ | CH₃ |
| F | NHSO₂C₄H₉-n | CH₃ | C₂F₅ | CH₃ |
| F | NHSO₂C₄H₉-sec | CH₃ | C₂F₅ | CH₃ |
| F | NHSO₂C₄H₉-iso | CH₃ | C₂F₅ | CH₃ |
| F | NHSO₂C₅H₁₁-n | CH₃ | C₂F₅ | CH₃ |
| F | NHSO₂-C₆H₅ | CH₃ | C₂F₅ | CH₃ |
| F | NHSO₂-C₆H₄-CH₃ (para) | CH₃ | C₂F₅ | CH₃ |
| F | NHSO₂CH₃ | Cl | C₂F₅ | CH₃ |
| F | NHSO₂CF₃ | Cl | C₂F₅ | CH₃ |
| F | NHSO₂C₂H₅ | Cl | C₂F₅ | CH₃ |
| F | NHSO₂CH₂CF₃ | Cl | C₂F₅ | CH₃ |
| F | NHSO₂C₃H₇-n | Cl | C₂F₅ | CH₃ |
| F | NHSO₂C₃H₇-i | Cl | C₂F₅ | CH₃ |
| F | NHSO₂-cyclopropyl | Cl | C₂F₅ | CH₃ |
| F | NHSO₂CH₂CH₂CH₂Cl | Cl | C₂F₅ | CH₃ |
| F | NHSO₂C₄H₉-n | Cl | C₂F₅ | CH₃ |
| F | NHSO₂C₄H₉-sec | Cl | C₂F₅ | CH₃ |
| F | NHSO₂C₄H₉-iso | Cl | C₂F₅ | CH₃ |
| F | NHSO₂C₅H₁₁-n | Cl | C₂F₅ | CH₃ |
| F | NHSO₂-C₆H₅ | Cl | C₂F₅ | CH₃ |
| F | NHSO₂-C₆H₄-CH₃ (para) | Cl | C₂F₅ | CH₃ |
| F | NHSO₂CH₃ | F | C₂F₅ | CH₃ |
| F | NHSO₂CF₃ | F | C₂F₅ | CH₃ |
| F | NHSO₂C₂H₅ | F | C₂F₅ | CH₃ |
| F | NHSO₂CH₂CF₃ | F | C₂F₅ | CH₃ |

TABLE 1-continued

Examples of the compounds of the formula (IA)

| $R^1$ | $R^2$ | $R^3$ | $R^4$ | $R^5$ |
|---|---|---|---|---|
| F | NHSO$_2$C$_3$H$_7$-n | F | C$_2$F$_5$ | CH$_3$ |
| F | NHSO$_2$C$_3$H$_7$-i | F | C$_2$F$_5$ | CH$_3$ |
| F | NHSO$_2$-cyclopropyl | F | C$_2$F$_5$ | CH$_3$ |
| F | NHSO$_2$CH$_2$CH$_2$CH$_2$Cl | F | C$_2$F$_5$ | CH$_3$ |
| F | NHSO$_2$C$_4$H$_9$-n | F | C$_2$F$_5$ | CH$_3$ |
| F | NHSO$_2$C$_4$H$_9$-sec | F | C$_2$F$_5$ | CH$_3$ |
| F | NHSO$_2$C$_4$H$_9$-iso | F | C$_2$F$_5$ | CH$_3$ |
| F | NHSO$_2$C$_5$H$_{11}$-n | F | C$_2$F$_5$ | CH$_3$ |
| F | NHSO$_2$-phenyl | F | C$_2$F$_5$ | CH$_3$ |
| F | NHSO$_2$-(4-CH$_3$-phenyl) | F | C$_2$F$_5$ | CH$_3$ |
| F | N(CH$_3$)SO$_2$CH$_3$ | CH$_3$ | C$_2$F$_5$ | CH$_3$ |
| F | N(CH$_3$)SO$_2$CF$_3$ | CH$_3$ | C$_2$F$_5$ | CH$_3$ |
| F | N(CH$_3$)SO$_2$C$_2$H$_5$ | CH$_3$ | C$_2$F$_5$ | CH$_3$ |
| F | N(CH$_3$)SO$_2$CH$_2$CF$_3$ | CH$_3$ | C$_2$F$_5$ | CH$_3$ |
| F | N(CH$_3$)SO$_2$C$_3$H$_7$-n | CH$_3$ | C$_2$F$_5$ | CH$_3$ |
| F | N(CH$_3$)SO$_2$C$_3$H$_7$-i | CH$_3$ | C$_2$F$_5$ | CH$_3$ |
| F | N(CH$_3$)SO$_2$-cyclopropyl | CH$_3$ | C$_2$F$_5$ | CH$_3$ |
| F | N(CH$_3$)SO$_2$C$_4$H$_9$-n | CH$_3$ | C$_2$F$_5$ | CH$_3$ |
| F | N(CH$_3$)SO$_2$C$_4$H$_9$-sec | CH$_3$ | C$_2$F$_5$ | CH$_3$ |
| F | N(CH$_3$)SO$_2$C$_4$H$_9$-iso | CH$_3$ | C$_2$F$_5$ | CH$_3$ |
| F | N(CH$_3$)SO$_2$-phenyl | CH$_3$ | C$_2$F$_5$ | CH$_3$ |
| F | N(CH$_3$)SO$_2$-(4-CH$_3$-phenyl) | CH$_3$ | C$_2$F$_5$ | CH$_3$ |
| F | N(CH$_3$)SO$_2$CH$_3$ | Cl | C$_2$F$_5$ | CH$_3$ |
| F | N(CH$_3$)SO$_2$CF$_3$ | Cl | C$_2$F$_5$ | CH$_3$ |
| F | N(CH$_3$)SO$_2$C$_2$H$_5$ | Cl | C$_2$F$_5$ | CH$_3$ |
| F | N(CH$_3$)SO$_2$CH$_2$CF$_3$ | Cl | C$_2$F$_5$ | CH$_3$ |
| F | N(CH$_3$)SO$_2$C$_3$H$_7$-n | Cl | C$_2$F$_5$ | CH$_3$ |
| F | N(CH$_3$)SO$_2$C$_3$H$_7$-i | Cl | C$_2$F$_5$ | CH$_3$ |
| F | N(CH$_3$)SO$_2$-cyclopropyl | Cl | C$_2$F$_5$ | CH$_3$ |
| F | N(CH$_3$)SO$_2$C$_4$H$_9$-n | Cl | C$_2$F$_5$ | CH$_3$ |
| F | N(CH$_3$)SO$_2$C$_4$H$_9$-sec | Cl | C$_2$F$_5$ | CH$_3$ |
| F | N(CH$_3$)SO$_2$C$_4$H$_9$-iso | Cl | C$_2$F$_5$ | CH$_3$ |
| F | N(CH$_3$)SO$_2$-phenyl | Cl | C$_2$F$_5$ | CH$_3$ |
| F | N(CH$_3$)SO$_2$-(4-CH$_3$-phenyl) | Cl | C$_2$F$_5$ | CH$_3$ |
| F | N(CH$_3$)SO$_2$CH$_3$ | F | C$_2$F$_5$ | CH$_3$ |

TABLE 1-continued

Examples of the compounds of the formula (IA)

| $R^1$ | $R^2$ | $R^3$ | $R^4$ | $R^5$ |
|---|---|---|---|---|
| F | N(CH$_3$)—SO$_2$CF$_3$ | F | $C_2F_5$ | $CH_3$ |
| F | N(CH$_3$)—SO$_2$C$_2$H$_5$ | F | $C_2F_5$ | $CH_3$ |
| F | N(CH$_3$)—SO$_2$CH$_2$CF$_3$ | F | $C_2F_5$ | $CH_3$ |
| F | N(CH$_3$)—SO$_2$C$_3$H$_7$-n | F | $C_2F_5$ | CR3 |
| F | N(CH$_3$)—SO$_2$C$_3$H$_7$-i | F | $C_2F_5$ | $CH_3$ |
| F | N(CH$_3$)—SO$_2$-cyclopropyl | F | $C_2F_5$ | $CH_3$ |
| F | N(CH$_3$)—SO$_2$C$_4$H$_9$-n | F | $C_2F_5$ | $CH_3$ |
| F | N(CH$_3$)—SO$_2$C$_4$H$_9$-sec | F | $C_2F_5$ | $CH_3$ |
| F | N(CH$_3$)—SO$_2$C$_4$H$_9$-iso | F | $C_2F_5$ | $CH_3$ |
| F | N(CH$_3$)—SO$_2$-phenyl | F | $C_2F_5$ | $CH_3$ |
| F | N(CH$_3$)—SO$_2$-(4-CH$_3$-phenyl) | F | $C_2F_5$ | $CH_3$ |
| F | NHSO$_2$CH$_3$ | H | $C_2F_5$ | $CHF_2$ |
| F | NHSO$_2$CF$_3$ | H | $C_2F_5$ | $CHF_2$ |
| F | NHSO$_2$C$_2$H$_5$ | H | $C_2F_5$ | $CHF_2$ |
| F | NHSO$_2$CH$_2$CF$_3$ | H | $C_2F_5$ | $CHF_2$ |
| P | NHSO$_2$C$_3$H$_7$-n | H | $C_2F_5$ | $CHF_2$ |
| F | NHSO$_2$C$_3$H$_7$-i | H | $C_2F_5$ | $CHF_2$ |
| F | NHSO$_2$-cyclopropyl | H | $C_2F_5$ | $CHF_2$ |
| F | NHSO$_2$CH$_2$CH$_2$CH$_2$Cl | H | $C_2F_5$ | $CHF_2$ |
| F | NHSO$_2$C$_4$H$_9$-n | H | $C_2F_5$ | $CHF_2$ |
| F | NHSO$_2$C$_4$H$_9$-sec | H | $C_2F_5$ | $CHF_2$ |
| F | NHSO$_2$C$_4$H$_9$-iso | H | $C_2F_5$ | $CHF_2$ |
| F | NHSO$_2$C$_5$H$_{11}$-n | H | $C_2F_5$ | $CHF_2$ |
| F | NHSO$_2$-phenyl | H | $C_2F_5$ | $CHF_2$ |
| F | NHSO$_2$-(4-CH$_3$-phenyl) | H | $C_2F_5$ | $CHF_2$ |
| F | N(CH$_3$)—SO$_2$CH$_3$ | H | $C_2F_5$ | $CHF_2$ |
| F | N(CH$_3$)—SO$_2$CF$_3$ | H | $C_2F_5$ | $CHF_2$ |
| F | N(CH$_3$)—SO$_2$C$_2$H$_5$ | H | $C_2F_5$ | $CHF_2$ |
| F | N(CH$_3$)—SO$_2$CH$_2$CF$_3$ | H | $C_2F_5$ | $CHF_2$ |
| F | N(CH$_3$)—SO$_2$C$_3$H$_7$-n | H | $C_2F_5$ | $CHF_2$ |
| F | N(CH$_3$)—SO$_2$C$_3$H$_7$-i | H | $C_2F_5$ | $CHF_2$ |
| F | N(CH$_3$)—SO$_2$-cyclopropyl | H | $C_2F_5$ | $CHF_2$ |
| F | N(CH$_3$)—SO$_2$C$_4$H$_9$-n | H | $C_2F_5$ | $CHF_2$ |
| F | N(CH$_3$)—SO$_2$C$_4$H$_9$-sec | H | $C_2F_5$ | $CHF_2$ |
| F | N(CH$_3$)—SO$_2$C$_4$H$_9$-iso | H | $C_2F_5$ | $CHF_2$ |
| F | N(CH$_3$)—SO$_2$C$_5$H$_{10}$-n | H | $C_2F_5$ | $CHF_2$ |
| F | N(CH$_3$)—SO$_2$-phenyl | H | $C_2F_5$ | $CHF_2$ |
| F | N(CH$_3$)—SO$_2$-(4-CH$_3$-phenyl) | H | $C_2F_5$ | $CHF_2$ |

TABLE 1-continued

Examples of the compounds of the formula (IA)

| R¹ | R² | R³ | R⁴ | R⁵ |
|---|---|---|---|---|
| F | NHSO$_2$CH$_3$ | CH$_3$ | C$_2$F$_5$ | CHF$_2$ |
| F | NHSO$_2$CF$_3$ | CH$_3$ | C$_2$F$_5$ | CHF$_2$ |
| F | NHSO$_2$C$_2$H$_5$ | CH$_3$ | C$_2$F$_5$ | CHF$_2$ |
| F | NHSO$_2$CH$_2$CF$_3$ | CH$_3$ | C$_2$F$_5$ | CHF$_2$ |
| F | NHSO$_2$C$_3$H$_7$-n | CH$_3$ | C$_2$F$_5$ | CHF$_2$ |
| F | NHSO$_2$C$_3$H$_7$-i | CH$_3$ | C$_2$F$_5$ | CHF$_2$ |
| F | NHSO$_2$-cyclopropyl  | CH$_3$ | C$_2$F$_5$ | CHF$_2$ |
| F | NHSO$_2$CH$_2$CH$_2$CH$_2$Cl | CH$_3$ | C$_2$F$_5$ | CHF$_2$ |
| F | NHSO$_2$C$_4$H$_9$-n | CH$_3$ | C$_2$F$_5$ | CHF$_2$ |
| F | NHSO$_2$C$_4$H$_9$-sec | CH$_3$ | C$_2$F$_5$ | CHF$_2$ |
| F | NHSO$_2$C$_4$H$_9$-iso | CH$_3$ | C$_2$F$_5$ | CHF$_2$ |
| F | NHSO$_2$C$_5$H$_{11}$-n | CH$_3$ | C$_2$F$_5$ | CHF$_2$ |
| F | NHSO$_2$-phenyl  | CH$_3$ | C$_2$F$_5$ | CHF$_2$ |
| F | NHSO$_2$-(4-methylphenyl)  | CH$_3$ | C$_2$F$_5$ | CHF$_2$ |
| H | NHSO$_2$CH$_3$ | H | CF$_2$Cl | CH$_3$ |
| H | NHSO$_2$CF$_3$ | H | CF$_2$Cl | CH$_3$ |
| H | NHSO$_2$C$_2$H$_5$ | H | CF$_2$Cl | CH$_3$ |
| H | NHSO$_2$CH$_2$CF$_3$ | H | CF$_2$Cl | CH$_3$ |
| H | NHSO$_2$C$_3$H$_7$-n | H | CF$_2$Cl | CH$_3$ |
| H | NHSO$_2$C$_3$H$_7$-i | H | CF$_2$Cl | CH$_3$ |
| H | NHSO$_2$-cyclopropyl  | H | CF$_2$Cl | CH$_3$ |
| H | NHSO$_2$CH$_2$CH$_2$CH$_2$Cl | H | CF$_2$Cl | CH$_3$ |
| H | NHSO$_2$C$_4$H$_9$-n | H | CF$_2$Cl | CH$_3$ |
| H | NHSO$_2$C$_4$H$_9$-sec | H | CF$_2$Cl | CH$_3$ |
| H | NHSO$_2$C$_4$H$_9$-iso | H | CF$_2$Cl | CH$_3$ |
| H | NHSO$_2$C$_5$H$_{11}$-n | H | CF$_2$Cl | CH$_3$ |
| H | NHSO$_2$-phenyl  | H | CF$_2$Cl | CH$_3$ |
| H | NHSO$_2$-(4-methylphenyl)  | H | CF$_2$Cl | CH$_3$ |
| F | NHSO$_2$CH$_3$ | H | CF$_2$Cl | CH$_3$ |
| F | NHSO$_2$CF$_3$ | H | CF$_2$Cl | CH$_3$ |
| F | NHSO$_2$C$_2$H$_5$ | H | CF$_2$Cl | CH$_3$ |
| F | NHSO$_2$CH$_2$CF$_3$ | H | CF$_2$Cl | CH$_3$ |
| F | NHSO$_2$C$_3$H$_7$-n | H | CF$_2$Cl | CH$_3$ |
| F | NHSO$_2$C$_3$H$_7$-i | H | CF$_2$Cl | CH$_3$ |
| F | NHSO$_2$-cyclopropyl  | H | CF$_2$Cl | CH$_3$ |
| F | NHSO$_2$CH$_2$CH$_2$CH$_2$Cl | H | CF$_2$Cl | CH$_3$ |
| F | NHSO$_2$C$_4$H$_9$-n | H | CF$_2$Cl | CH$_3$ |
| F | NHSO$_2$C$_4$H$_9$-sec | H | CF$_2$Cl | CH$_3$ |
| F | NHSO$_2$C$_4$H$_9$-iso | H | CF$_2$Cl | CH$_3$ |
| F | NHSO$_2$C$_5$H$_{11}$-n | H | CF$_2$Cl | CH$_3$ |
| F | NHSO$_2$-phenyl 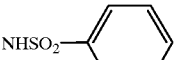 | H | CF$_2$Cl | CH$_3$ |
| F | NHSO$_2$-(4-methylphenyl)  | H | CF$_2$Cl | CH$_3$ |
| H | N(CH$_3$)SO$_2$CH$_3$ | H | CF$_2$Cl | CH$_3$ |
| H | N(CH$_3$)SO$_2$CF$_3$ | H | CF$_2$Cl | CH$_3$ |
| H | N(CH$_3$)SO$_2$C$_2$H$_5$ | H | CF$_2$Cl | CH$_3$ |
| H | N(CH$_3$)SO$_2$CH$_2$CF$_3$ | H | CF$_2$Cl | CH$_3$ |
| H | N(CH$_3$)SO$_2$C$_3$H$_7$-n | H | CF$_2$Cl | CH$_3$ |
| H | N(CH$_3$)SO$_2$C$_3$H$_7$-i | H | CF$_2$Cl | CH$_3$ |
| H | N(CH$_3$)SO$_2$-cyclopropyl 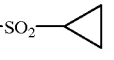 | H | CF$_2$Cl | CH$_3$ |
| H | N(CH$_3$)SO$_2$C$_4$H$_9$-n | H | CF$_2$Cl | CH$_3$ |
| H | N(CH$_3$)SO$_2$C$_4$H$_9$-sec | H | CF$_2$Cl | CH$_3$ |
| H | N(CH$_3$)SO$_2$C$_4$H$_9$-iso | H | CF$_2$Cl | CH$_3$ |
| H | N(CH$_3$)SO$_2$C$_5$H$_{10}$-n | H | CF$_2$Cl | CH$_3$ |
| H | N(CH$_3$)SO$_2$-phenyl 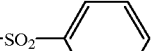 | H | CF$_2$Cl | CH$_3$ |
| H | N(CH$_3$)SO$_2$-(4-methylphenyl) 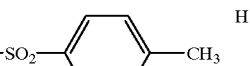 | H | CF$_2$Cl | CH$_3$ |

TABLE 1-continued

Examples of the compounds of the formula (IA)

| R¹ | R² | R³ | R⁴ | R⁵ |
|---|---|---|---|---|
| F | N(CH₃)—SO₂CH₃ | H | CF₂Cl | CH₃ |
| F | N(CH₃)—SO₂CF₃ | H | CF₂Cl | CH₃ |
| F | N(CH₃)—SO₂C₂H₅ | H | CF₂Cl | CH₃ |
| F | N(CH₃)—SO₂CH₂CF₃ | H | CF₂Cl | CH₃ |
| F | N(CH₃)—SO₂C₃H₇-n | H | CF₂Cl | CH₃ |
| F | N(CH₃)—SO₂C₃H₇-i | H | CF₂Cl | CH₃ |
| F | N(CH₃)—SO₂-cyclopropyl | H | CF₂Cl | CH₃ |
| F | N(CH₃)—SO₂C₄H₉-n | H | CF₂Cl | CH₃ |
| F | N(CH₃)—SO₂C₄H₉-sec | H | CF₂Cl | CH₃ |
| F | N(CH₃)—SO₂C₄H₉-iso | H | CF₂Cl | CH₃ |
| F | N(CH₃)—SO₂C₅H₁₀-n | H | CF₂Cl | CH₃ |
| F | N(CH₃)—SO₂-phenyl | H | CF₂Cl | CH₃ |
| F | N(CH₃)—SO₂-(4-CH₃-phenyl) | H | CF₂Cl | CH₃ |
| H | N(C₂H₅)—SO₂CH₃ | H | CF₂Cl | CH₃ |
| H | N(C₂H₅)—SO₂CF₃ | H | CF₂Cl | CH₃ |
| H | N(C₂H₅)—SO₂C₂H₅ | H | CF₂Cl | CH₃ |
| H | N(C₂H₅)—SO₂CH₂CF₃ | H | CF₂Cl | CH₃ |
| H | N(C₂H₅)—SO₂C₃H₇-n | H | CF₂Cl | CH₃ |
| H | N(C₂H₅)—SO₂C₃H₇-i | H | CF₂Cl | CH₃ |
| H | N(C₂H₅)—SO₂-cyclopropyl | H | CF₂Cl | CH₃ |
| H | N(C₂H₅)—SO₂C₄H₉-n | H | CF₂Cl | CH₃ |
| H | N(C₂H₅)—SO₂C₄H₉-sec | H | CF₂Cl | CH₃ |
| H | N(C₂H₅)—SO₂C₄H₉-iso | H | CF₂Cl | CH₃ |
| H | N(C₂H₅)—SO₂C₅H₁₀-n | H | CF₂Cl | CH₃ |
| H | N(C₂H₅)—SO₂-phenyl | H | CF₂Cl | CH₃ |
| H | N(C₂H₅)—SO₂-(4-CH₃-phenyl) | H | CF₂Cl | CH₃ |
| F | N(C₂H₅)—SO₂CH₃ | H | CF₂Cl | CH₃ |
| F | N(C₂H₅)—SO₂CF₃ | H | CF₂Cl | CH₃ |
| F | N(C₂H₅)—SO₂C₂H₅ | H | CF₂Cl | CH₃ |
| F | N(C₂H₅)—SO₂CH₂CF₃ | H | CF₂Cl | CH₃ |

TABLE 1-continued

Examples of the compounds of the formula (IA)

| R¹ | R² | R³ | R⁴ | R⁵ |
|---|---|---|---|---|
| F | N(C₂H₅)—SO₂C₃H₇-n | H | CF₂Cl | CH₃ |
| F | N(C₂H₅)—SO₂C₃H₇-i | H | CF₂Cl | CH₃ |
| F | N(C₂H₅)—SO₂-cyclopropyl | H | CF₂Cl | CH₃ |
| F | N(C₂H₅)—SO₂C₄H₉-n | H | CF₂Cl | CH₃ |
| F | N(C₂H₅)—SO₂C₄H₉-sec | H | CF₂Cl | CH₃ |
| F | N(C₂H₅)—SO₂C₄H₉-iso | H | CF₂Cl | CH₃ |
| F | N(C₂H₅)—SO₂C₅H₁₀-n | H | CF₂Cl | CH₃ |
| F | N(C₂H₅)—SO₂-phenyl | H | CF₂Cl | CH₃ |
| F | N(C₂H₅)—SO₂-(4-CH₃-phenyl) | H | CF₂Cl | CH₃ |
| F | N(C₂H₅)—SO₂CH₃ | H | CF₂Cl | C₂H₅ |
| F | N(C₂H₅)—SO₂CF₃ | H | CF₂Cl | C₂H₅ |
| F | N(C₂H₅)—SO₂C₂H₅ | H | CF₂Cl | C₂H₅ |
| F | N(C₂H₅)—SO₂CH₂CF₃ | H | CF₂Cl | C₂H₅ |
| F | N(C₂H₅)—SO₂C₃H₇-n | H | CF₂Cl | C₂H₅ |
| F | N(C₂H₅)—SO₂C₃H₇-i | H | CF₂Cl | C₂H₅ |
| F | N(C₂H₅)—SO₂-cyclopropyl | H | CF₂Cl | C₂H₅ |
| F | N(C₂H₅)—SO₂C₄H₉-n | H | CF₂Cl | C₂H₅ |
| F | N(C₂H₅)—SO₂C₄H₉-sec | H | CF₂Cl | C₂H₅ |
| F | N(C₂H₅)—SO₂C₄H₉-iso | H | CF₂Cl | C₂H₅ |
| F | N(C₂H₅)—SO₂C₅H₁₀-n | H | CF₂Cl | C₂H₅ |
| F | N(C₂H₅)—SO₂-phenyl | H | CF₂Cl | C₂H₅ |
| F | N(C₂H₅)—SO₂-(4-CH₃-phenyl) | H | CF₂Cl | C₂H₅ |
| H | NHSO₂CH₃ | H | CF₂Cl | C₂H₅ |
| H | NHSO₂CF₃ | H | CF₂Cl | C₂H₅ |
| H | NHSO₂C₂H₅ | H | CF₂Cl | C₂H₅ |
| H | NHSO₂CH₂CF₃ | H | CF₂Cl | C₂H₅ |
| H | NHSO₂C₃H₇-n | H | CF₂Cl | C₂H₅ |
| H | NHSO₂C₃H₇-i | H | CF₂Cl | C₂H₅ |
| H | NHSO₂-cyclopropyl | H | CF₂Cl | C₂H₅ |
| H | NHSO₂CH₂CH₂CH₂Cl | H | CF₂Cl | C₂H₅ |
| H | NHSO₂C₄H₉-n | H | CF₂Cl | C₂H₅ |
| H | NHSO₂C₄H₉-sec | H | CF₂Cl | C₂H₅ |
| H | NHSO₂C₄H₉-iso | H | CF₂Cl | C₂H₅ |
| H | NHSO₂C₅H₁₁-n | H | CF₂Cl | C₂H₅ |
| H | NHSO₂-phenyl | H | CF₂Cl | C₂H₅ |
| H | NHSO₂-(4-CH₃-phenyl) | H | CF₂Cl | C₂H₅ |
| F | NHSO₂CH₃ | H | CF₂Cl | C₂H₅ |
| F | NHSO₂CF₃ | H | CF₂Cl | C₂H₅ |
| F | NHSO₂C₂H₅ | H | CF₂Cl | C₂H₅ |
| F | NHSO₂CH₂CF₃ | H | CF₂Cl | C₂H₅ |
| F | NHSO₂C₃H₇-n | H | CF₂Cl | C₂H₅ |
| F | NHSO₂C₃H₇-i | H | CF₂Cl | C₂H₅ |
| F | NHSO₂-cyclopropyl | H | CF₂Cl | C₂H₅ |

TABLE 1-continued

Examples of the compounds of the formula (IA)

| R¹ | R² | R³ | R⁴ | R⁵ |
|---|---|---|---|---|
| F | $NHSO_2CH_2CH_2CH_2Cl$ | H | $CF_2Cl$ | $C_2H_5$ |
| F | $NHSO_2C_4H_9$-n | H | $CF_2Cl$ | $C_2H_5$ |
| F | $NHSO_2C_4H_9$-sec | H | $CF_2Cl$ | $C_2H_5$ |
| F | $NHSO_2C_4H_9$-iso | H | $CF_2Cl$ | $C_2H_5$ |
| F | $NHSO_2C_5H_{11}$-n | H | $CF_2Cl$ | $C_2H_5$ |
| F | $NHSO_2$–C₆H₅ | H | $CF_2Cl$ | $C_2H_5$ |
| F | $NHSO_2$–C₆H₄–CH₃ | H | $CF_2Cl$ | $C_2H_5$ |
| H | $NHSO_2CH_3$ | $CH_3$ | $CF_2Cl$ | $CH_3$ |
| H | $NHSO_2CF_3$ | $CH_3$ | $CF_2Cl$ | $CH_3$ |
| H | $NHSO_2C_2H_5$ | $CH_3$ | $CF_2Cl$ | $CH_3$ |
| H | $NHSO_2CH_2CF_3$ | $CH_3$ | $CF_2Cl$ | $CH_3$ |
| H | $NHSO_2C_3H_7$-n | $CH_3$ | $CF_2Cl$ | $CH_3$ |
| H | $NHSO_2C_3H_7$-i | $CH_3$ | $CF_2Cl$ | $CH_3$ |
| H | $NHSO_2$–cyclopropyl | $CH_3$ | $CF_2Cl$ | $CH_3$ |
| H | $NHSO_2CH_2CH_2CH_2Cl$ | $CH_3$ | $CF_2Cl$ | $CH_3$ |
| H | $NHSO_2C_4H_9$-n | $CH_3$ | $CF_2Cl$ | $CH_3$ |
| H | $NHSO_2C_4H_9$-sec | $CH_3$ | $CF_2Cl$ | $CH_3$ |
| H | $NHSO_2C_4H_9$-iso | $CH_3$ | $CF_2Cl$ | $CH_3$ |
| H | $NHSO_2C_5H_{11}$-n | $CH_3$ | $CF_2Cl$ | $CH_3$ |
| H | $NHSO_2$–C₆H₅ | $CH_3$ | $CF_2Cl$ | $CH_3$ |
| H | $NHSO_2$–C₆H₄–CH₃ | $CH_3$ | $CF_2Cl$ | $CH_3$ |
| F | $NHSO_2CH_3$ | $CH_3$ | $CF_2Cl$ | $CH_3$ |
| F | $NHSO_2CF_3$ | $CH_3$ | $CF_2Cl$ | $CH_3$ |
| F | $NHSO_2C_2H_5$ | $CH_3$ | $CF_2Cl$ | $CH_3$ |
| F | $NHSO_2CH_2CF_3$ | $CH_3$ | $CF_2Cl$ | $CH_3$ |
| F | $NHSO_2C_3H_7$-n | $CH_3$ | $CF_2Cl$ | $CH_3$ |
| F | $NHSO_2C_3H_7$-i | $CH_3$ | $CF_2Cl$ | $CH_3$ |
| F | $NHSO_2$–cyclopropyl | $CH_3$ | $CF_2Cl$ | $CH_3$ |
| F | $NHSO_2CH_2CH_2CH_2Cl$ | $CH_3$ | $CF_2Cl$ | $CH_3$ |
| F | $NHSO_2C_4H_9$-n | $CH_3$ | $CF_2Cl$ | $CH_3$ |
| F | $NHSO_2C_4H_9$-sec | $CH_3$ | $CF_2Cl$ | $CH_3$ |
| F | $NHSO_2C_4H_9$-iso | $CH_3$ | $CF_2Cl$ | $CH_3$ |
| F | $NHSO_2C_5H_{11}$-n | $CH_3$ | $CF_2Cl$ | $CH_3$ |
| F | $NHSO_2$–C₆H₅ | $CH_3$ | $CF_2Cl$ | $CH_3$ |
| F | $NHSO_2$–C₆H₄–CH₃ | $CH_3$ | $CF_2Cl$ | $CH_3$ |
| F | $NHSO_2CH_3$ | Cl | $CF_2Cl$ | $CH_3$ |
| F | $NHSO_2CF_3$ | Cl | $CF_2Cl$ | $CH_3$ |
| F | $NHSO_2C_2H_5$ | Cl | $CF_2Cl$ | $CH_3$ |
| F | $NHSO_2CH_2CF_3$ | Cl | $CF_2Cl$ | $CH_3$ |
| F | $NHSO_2C_3H_7$-n | Cl | $CF_2Cl$ | $CH_3$ |
| F | $NHSO_2C_3H_7$-i | Cl | $CF_2Cl$ | $CH_3$ |
| F | $NHSO_2$–cyclopropyl | Cl | $CF_2Cl$ | $CH_3$ |
| F | $NHSO_2CH_2CH_2CH_2Cl$ | Cl | $CF_2Cl$ | $CH_3$ |
| F | $NHSO_2C_4H_9$-n | Cl | $CF_2Cl$ | $CH_3$ |
| F | $NHSO_2C_4H_9$-sec | Cl | $CF_2Cl$ | $CH_3$ |
| F | $NHSO_2C_4H_9$-iso | Cl | $CF_2Cl$ | $CH_3$ |
| F | $NHSO_2C_5H_{11}$-n | Cl | $CF_2Cl$ | $CH_3$ |
| F | $NHSO_2$–C₆H₅ | Cl | $CF_2Cl$ | $CH_3$ |
| F | $NHSO_2$–C₆H₄–CH₃ | Cl | $CF_2Cl$ | $CH_3$ |
| F | $NHSO_2CH_3$ | F | $CF_2Cl$ | $CH_3$ |
| F | $NHSO_2CF_3$ | F | $CF_2Cl$ | $CH_3$ |
| F | $NHSO_2C_2H_5$ | F | $CF_2Cl$ | $CH_3$ |
| F | $NHSO_2CH_2CF_3$ | F | $CF_2Cl$ | $CH_3$ |
| F | $NHSO_2C_3H_7$-n | F | $CF_2Cl$ | $CH_3$ |
| F | $NHSO_2C_3H_7$-i | F | $CF_2Cl$ | $CH_3$ |
| F | $NHSO_2$–cyclopropyl | F | $CF_2Cl$ | $CH_3$ |
| F | $NHSO_2CH_2CH_2CH_2Cl$ | F | $CF_2Cl$ | $CH_3$ |
| F | $NHSO_2C_4H_9$-n | F | $CF_2Cl$ | $CH_3$ |
| F | $NHSO_2C_4H_9$-sec | F | $CF_2Cl$ | $CH_3$ |
| F | $NHSO_2C_4H_9$-iso | F | $CF_2Cl$ | $CH_3$ |
| F | $NHSO_2C_5H_{11}$-n | F | $CF_2Cl$ | $CH_3$ |
| F | $NHSO_2$–C₆H₅ | F | $CF_2Cl$ | $CH_3$ |
| F | $NHSO_2$–C₆H₄–CH₃ | F | $CF_2Cl$ | $CH_3$ |
| F | $N(CH_3)SO_2CH_3$ | $CH_3$ | $CF_2Cl$ | $CH_3$ |
| F | $N(CH_3)SO_2CF_3$ | $CH_3$ | $CF_2Cl$ | $CH_3$ |
| F | $N(CH_3)SO_2C_2H_5$ | $CH_3$ | $CF_2Cl$ | $CH_3$ |
| F | $N(CH_3)SO_2CH_2CF_3$ | $CH_3$ | $CF_2Cl$ | $CH_3$ |

TABLE 1-continued

Examples of the compounds of the formula (IA)

| R¹ | R² | R³ | R⁴ | R⁵ |
|---|---|---|---|---|
| F | N(CH₃)—SO₂C₃H₇-n | CH₃ | CF₂Cl | CH₃ |
| F | N(CH₃)—SO₂C₃H₇-i | CH₃ | CF₂Cl | CH₃ |
| F | N(CH₃)—SO₂-cyclopropyl | CH₃ | CF₂Cl | CH₃ |
| F | N(CH₃)—SO₂C₄H₉-n | CH₃ | CF₂Cl | CH₃ |
| F | N(CH₃)—SO₂C₄H₉-sec | CH₃ | CF₂Cl | CH₃ |
| F | N(CH₃)—SO₂C₄H₉-iso | CH₃ | CF₂Cl | CH₃ |
| F | N(CH₃)—SO₂—C₆H₅ | CH₃ | CF₂Cl | CH₃ |
| F | N(CH₃)—SO₂—C₆H₄—CH₃ | CH₃ | CF₂Cl | CH₃ |
| F | N(CH₃)—SO₂CH₃ | Cl | CF₂Cl | CH₃ |
| F | N(CH₃)—SO₂CF₃ | Cl | CF₂Cl | CH₃ |
| F | N(CH₃)—SO₂C₂H₅ | Cl | CF₂Cl | CH₃ |
| F | N(CH₃)—SO₂CH₂CF₃ | Cl | CF₂Cl | CH₃ |
| F | N(CH₃)—SO₂C₃H₇-n | Cl | CF₂Cl | CH₃ |
| F | N(CH₃)—SO₂C₃H₇-i | Cl | CF₂Cl | CH₃ |
| F | N(CH₃)—SO₂-cyclopropyl | Cl | CF₂Cl | CH₃ |
| F | N(CH₃)—SO₂C₄H₉-n | Cl | CF₂Cl | CH₃ |
| F | N(CH₃)—SO₂C₄H₉-sec | Cl | CF₂Cl | CH₃ |
| F | N(CH₃)—SO₂C₄H₉-iso | Cl | CF₂Cl | CH₃ |
| F | N(CH₃)—SO₂C₅H₁₀-n | Cl | CF₂Cl | CH₃ |
| F | N(CH₃)—SO₂—C₆H₅ | Cl | CF₂Cl | CH₃ |
| F | N(CH₃)—SO₂—C₆H₄—CH₃ | Cl | CF₂Cl | CH₃ |
| F | N(CH₃)—SO₂CH₃ | F | CF₂Cl | CH₃ |
| F | N(CH₃)—SO₂CF₃ | F | CF₂Cl | CH₃ |
| F | N(CH₃)—SO₂C₂H₅ | F | CF₂Cl | CH₃ |
| F | N(CH₃)—SO₂CH₂CF₃ | F | CF₂Cl | CH₃ |
| F | N(CH₃)—SO₂C₃H₇-n | F | CF₂Cl | CH₃ |
| F | N(CH₃)—SO₂C₃H₇-i | F | CF₂Cl | CH₃ |
| F | N(CH₃)—SO₂-cyclopropyl | F | CF₂Cl | CH₃ |
| F | N(CH₃)—SO₂C₄H₉-n | F | CF₂Cl | CH₃ |
| F | N(CH₃)—SO₂C₄H₉-sec | F | CF₂Cl | CH₃ |

TABLE 1-continued

Examples of the compounds of the formula (IA)

| R¹ | R² | R³ | R⁴ | R⁵ |
|---|---|---|---|---|
| F | N(CH₃)—SO₂C₄H₉-iso | F | CF₂Cl | CH₃ |
| F | N(CH₃)—SO₂—C₆H₅ | F | CF₂Cl | CH₃ |
| F | N(CH₃)—SO₂—C₆H₄—CH₃ | F | CF₂Cl | CH₃ |
| F | NHSO₂CH₃ | H | CF₂Cl | CHF₂ |
| F | NHSO₂CF₃ | H | CF₂Cl | CHF₂ |
| F | NHSO₂C₂H₅ | H | CF₂Cl | CHF₂ |
| F | NHSO₂CH₂CF₃ | H | CF₂Cl | CHF₂ |
| F | NHSO₂C₃H₇-n | H | CF₂Cl | CHF₂ |
| F | NHSO₂C₃H₇-i | H | CF₂Cl | CHF₂ |
| F | NHSO₂-cyclopropyl | H | CF₂Cl | CHF₂ |
| F | NHSO₂CH₂CH₂CH₂Cl | H | CF₂Cl | CHF₂ |
| F | NHSO₂C₄H₉-n | H | CF₂Cl | CHF₂ |
| F | NHSO₂C₄H₉-sec | H | CF₂Cl | CHF₂ |
| F | NHSO₂C₄H₉-iso | H | CF₂Cl | CHF₂ |
| F | NHSO₂C₅H₁₁-n | H | CF₂Cl | CHF₂ |
| F | NHSO₂—C₆H₅ | H | CF₂Cl | CHF₂ |
| F | NHSO₂—C₆H₄—CH₃ | H | CF₂Cl | CHF₂ |
| F | N(CH₃)—SO₂CH₃ | H | CF₂Cl | CHF₂ |
| F | N(CH₃)—SO₂CF₃ | H | CF₂Cl | CHF₂ |
| F | N(CH₃)—SO₂C₂H₅ | H | CF₂Cl | CHF₂ |
| F | N(CH₃)—SO₂CH₂CF₃ | H | CF₂Cl | CHF₂ |
| F | N(CH₃)—SO₂C₃H₇-n | H | CF₂Cl | CHF₂ |
| F | N(CH₃)—SO₂C₃H₇-i | H | CF₂Cl | CHF₂ |
| F | N(CH₃)—SO₂-cyclopropyl | H | CF₂Cl | CHF₂ |
| F | N(CH₃)—SO₂C₄H₉-n | H | CF₂Cl | CHF₂ |
| F | N(CH₃)—SO₂C₄H₉-sec | H | CF₂Cl | CHF₂ |
| F | N(CH₃)—SO₂C₄H₉-iso | H | CF₂Cl | CHF₂ |
| F | N(CH₃)—SO₂C₅H₁₀-n | H | CF₂Cl | CHF₂ |
| F | N(CH₃)—SO₂—C₆H₅ | H | CF₂Cl | CHF₂ |
| F | N(CH₃)—SO₂—C₆H₄—CH₃ | H | CF₂Cl | CHF₂ |
| F | NHSO₂CH₃ | CH₃ | CF₂Cl | CHF₂ |
| F | NHSO₂CF₃ | CH₃ | CF₂Cl | CHF₂ |
| F | NHSO₂C₂H₅ | CH₃ | CF₂Cl | CHF₂ |
| F | NHSO₂CH₂CF₃ | CH₃ | CF₂Cl | CHF₂ |
| F | NHSO₂C₃H₇-n | CH₃ | CF₂Cl | CHF₂ |
| F | NHSO₂C₃H₇-i | CH₃ | CF₂Cl | CHF₂ |
| F | NHSO₂-cyclopropyl | CH₃ | CF₂Cl | CHF₂ |
| F | NHSO₂CH₂CH₂CH₂Cl | CH₃ | CF₂Cl | CHF₂ |
| F | NHSO₂C₄H₉-n | CH₃ | CF₂Cl | CHF₂ |
| F | NHSO₂C₄H₉-sec | CH₃ | CF₂Cl | CHF₂ |
| F | NHSO₂C₄H₉-iso | CH₃ | CF₂Cl | CHF₂ |
| F | NHSO₂C₅H₁₁-n | CH₃ | CF₂Cl | CHF₂ |
| F | NHSO₂—C₆H₅ | CH₃ | CF₂Cl | CHF₂ |
| F | NHSO₂—C₆H₄—CH₃ | CH₃ | CF₂Cl | CHF₂ |
| H | —N(SO₂CH₃)₂ | H | CF₃ | CH₃ |
| H | —N(SO₂CH₃)(SO₂C₂H₅) | H | CF₃ | CH₃ |
| H | —N(SO₂C₂H₅)₂ | H | CF₃ | CH₃ |
| H | —N(SO₂CH₃)(SO₂C₃H₇) | H | CF₃ | CH₃ |
| H | —N(SO₂C₃H₇)₂ | H | CF₃ | CH₃ |
| H | —N(SO₂CH₃)(SO₂C₃H₇-i) | H | CF₃ | CH₃ |
| H | —N(SO₂C₃H₇-i)₂ | H | CF₃ | CH₃ |
| F | —N(SO₂CH₃)₂ | H | CF₃ | CH₃ |
| F | —N(SO₂CH₃)₂ | H | CF₃ | C₂H₅ |
| F | —N(SO₂CH₃)(SO₂C₂H₅) | H | CF₃ | CH₃ |
| F | —N(SO₂C₂H₅)₂ | H | CF₃ | CH₃ |

TABLE 1-continued

Examples of the compounds of the formula (IA)

| R¹ | R² | R³ | R⁴ | R⁵ |
|---|---|---|---|---|
| F | —N(SO$_2$CH$_3$)(SO$_2$C$_3$H$_7$) | H | CF$_3$ | CH$_3$ |
| F | —N(SO$_2$C$_3$H$_7$)$_2$ | H | CF$_3$ | CH$_3$ |
| F | —N(SO$_2$CH$_3$)(SO$_2$C$_3$H$_7$-i) | H | CF$_3$ | CH$_3$ |
| F | —N(SO$_2$C$_3$H$_7$-i)$_2$ | H | CF$_3$ | CH$_3$ |
| F | —N(SO$_2$C$_2$H$_5$)(SO$_2$C$_3$H$_7$) | H | CF$_3$ | CH$_3$ |
| F | 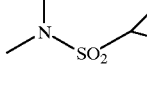 | H | CF$_3$ | CH$_3$ |
| F |  | H | CF$_3$ | CH$_3$ |
| F | —N(SO$_2$CH$_3$)(SO$_2$C$_4$H$_9$) | H | CF$_3$ | CH$_3$ |
| F | —N(SO$_2$C$_4$H$_9$)$_2$ | H | CF$_3$ | CH$_3$ |
| F | —N(SO$_2$CH$_3$)(SO$_2$CF$_3$) | H | CF$_3$ | CH$_3$ |
| F | —N(SO$_2$CF$_3$)$_2$ | H | CF$_3$ | CH$_3$ |
| F | —N(SO$_2$CH$_3$)(SO$_2$CH$_2$CF$_3$) | H | CF$_3$ | CH$_3$ |
| F | —N(SO$_2$CH$_2$CF$_3$)$_2$ | H | CF$_3$ | CH$_3$ |
| F | —N(SO$_2$CH$_3$)(SO$_2$C$_3$H$_6$Cl) | H | CF$_3$ | CH$_3$ |
| F | —N(SO$_2$CH$_2$CH$_2$CH$_2$Cl)$_2$ | H | CF$_3$ | CH$_3$ |
| F | —N(SO$_2$CH$_3$)(SO$_2$C$_6$H$_5$) | H | CF$_3$ | CH$_3$ |
| F | —N(SO$_2$C$_6$H$_5$)$_2$ | H | CF$_3$ | CH$_3$ |
| F | —N(SO$_2$C$_2$H$_5$)(SO$_2$C$_6$H$_5$) | H | CF$_3$ | CH$_3$ |
| F | 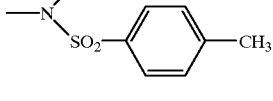 | H | CF$_3$ | CH$_3$ |
| F | —N(SO$_2$CH$_3$)$_2$ | H | CHF$_2$ | CH$_3$ |
| F | —N(SO$_2$CH$_3$)$_2$ | H | CHF$_2$ | C$_2$H$_5$ |
| F | —N(SO$_2$C$_2$H$_5$)$_2$ | H | CHF$_2$ | CH$_3$ |
| F | —N(SO$_2$CH$_3$)(SO$_2$C$_3$H$_7$) | H | CHF$_2$ | CH$_3$ |
| F | —N(SO$_2$C$_3$H$_7$)$_2$ | H | CHF$_2$ | CH$_3$ |
| F | —N(SO$_2$CH$_3$)(SO$_2$C$_3$H$_7$-i) | H | CHF$_2$ | CH$_3$ |
| F | —N(SO$_2$C$_3$H$_7$-i)$_2$ | H | CHF$_2$ | CH$_3$ |
| F | 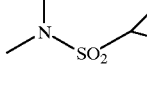 | H | CHF$_2$ | CH$_3$ |
| F |  | H | CHF$_2$ | CH$_3$ |
| F | —N(SO$_2$CH$_3$)(SO$_2$C$_4$H$_9$) | H | CHF$_2$ | CH$_3$ |
| F | —N(SO$_2$C$_4$H$_9$)$_2$ | H | CHF$_2$ | CH$_3$ |
| F | —N(SO$_2$CH$_3$)(SO$_2$CF$_3$) | H | CHF$_2$ | CH$_3$ |
| F | —N(SO$_2$CF$_3$)$_2$ | H | CHF$_2$ | CH$_3$ |
| F | —N(SO$_2$CH$_3$)(SO$_2$CH$_2$CF$_3$) | H | CHF$_2$ | CH$_3$ |
| F | —N(SO$_2$CH$_2$CF$_3$)$_2$ | H | CHF$_2$ | CH$_3$ |
| F | —N(SO$_2$CH$_3$)(SO$_2$C$_6$H$_5$) | H | CHF$_2$ | CH$_3$ |
| F | —N(SO$_2$C$_6$H$_5$)$_2$ | H | CHF$_2$ | CH$_3$ |
| F | —N(SO$_2$C$_2$H$_5$)(SO$_2$C$_6$H$_5$) | H | CHF$_2$ | CH$_3$ |
| F | 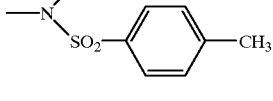 | H | CHF$_2$ | CH$_3$ |
| F | —N(SO$_2$CH$_3$)$_2$ | H | CF$_2$Cl | CH$_3$ |
| F | —N(SO$_2$CH$_3$)$_2$ | H | CF$_2$Cl | C$_2$H$_5$ |
| F | —N(SO$_2$C$_2$H$_5$)$_2$ | H | CF$_2$Cl | CH$_3$ |
| F | —N(SO$_2$CH$_3$)(SO$_2$C$_3$H$_7$) | H | CF$_2$Cl | CH$_3$ |
| F | —N(SO$_2$C$_3$H$_7$)$_2$ | H | CF$_2$Cl | CH$_3$ |
| F | —N(SO$_2$CH$_3$)(SO$_2$C$_3$H$_7$-i) | H | CF$_2$Cl | CH$_3$ |
| F | —N(SO$_2$C$_3$H$_7$-i)$_2$ | H | CF$_2$Cl | CH$_3$ |
| F | 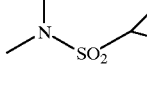 | H | CF$_2$Cl | CH$_3$ |
| F |  | H | CF$_2$Cl | CH$_3$ |
| F | —N(SO$_2$CH$_3$)(SO$_2$C$_4$H$_9$) | H | CF$_2$Cl | CH$_3$ |
| F | —N(SO$_2$C$_4$H$_9$)$_2$ | H | CF$_2$Cl | CH$_3$ |
| F | —N(SO$_2$CH$_3$)(SO$_2$CF$_3$) | H | CF$_2$Cl | CH$_3$ |
| F | —N(SO$_2$CF$_3$)$_2$ | H | CF$_2$Cl | CH$_3$ |
| F | —N(SO$_2$CH$_3$)(SO$_2$CH$_2$CF$_3$) | H | CF$_2$Cl | CH$_3$ |
| F | —N(SO$_2$CH$_2$CF$_3$)$_2$ | H | CF$_2$Cl | CH$_3$ |
| F | —N(SO$_2$CH$_2$CH$_2$CH$_2$Cl)$_2$ | H | CF$_2$Cl | CH$_3$ |
| F | —N(SO$_2$CH$_3$)(SO$_2$C$_6$H$_5$) | H | CF$_2$Cl | CH$_3$ |
| F | —N(SO$_2$C$_6$H$_5$)$_2$ | H | CF$_2$Cl | CH$_3$ |
| F | 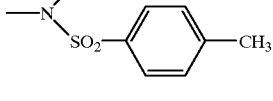 | H | CF$_2$Cl | CH$_3$ |
| F | —N(SO$_2$CH$_3$)$_2$ | H | C$_2$F$_5$ | CH$_3$ |
| F | —N(SO$_2$CH$_3$)$_2$ | H | C$_2$F$_5$ | C$_2$H$_5$ |
| F | —N(SO$_2$C$_2$H$_5$)$_2$ | H | C$_2$F$_5$ | CH$_3$ |
| F | —N(SO$_2$CH$_3$)(SO$_2$C$_3$H$_7$) | H | C$_2$F$_5$ | CH$_3$ |
| F | —N(SO$_2$C$_3$H$_7$)$_2$ | H | C$_2$F$_5$ | CH$_3$ |
| F | —N(SO$_2$CH$_3$)(SO$_2$C$_3$H$_7$-i) | H | C$_2$F$_5$ | CH$_3$ |
| F | —N(SO$_2$C$_3$H$_7$-i)$_2$ | H | C$_2$F$_5$ | CH$_3$ |
| F | 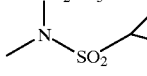 | H | C$_2$F$_5$ | CH$_3$ |
| F | —N(SO$_2$CH$_3$)(SO$_2$C$_4$H$_9$) | H | C$_2$F$_5$ | CH$_3$ |
| F | —N(SO$_2$C$_4$H$_9$)$_2$ | H | C$_2$F$_5$ | CH$_3$ |
| F | —N(SO$_2$CH$_3$)(SO$_2$CF$_3$) | H | C$_2$F$_5$ | CH$_3$ |
| F | —N(SO$_2$CF$_3$)$_2$ | H | C$_2$F$_5$ | CH$_3$ |
| F | —N(SO$_2$CH$_2$CF$_3$)$_2$ | H | C$_2$F$_5$ | CH$_3$ |
| F | —N(SO$_2$CH$_3$)(SO$_2$C$_6$H$_5$) | H | C$_2$F$_5$ | CH$_3$ |
| F | —N(SO$_2$C$_6$H$_5$)$_2$ | H | C$_2$F$_5$ | CH$_3$ |
| F | 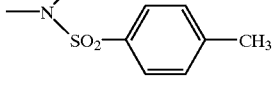 | H | C$_2$F$_5$ | CH$_3$ |
| F | —N(SO$_2$CH$_3$)$_2$ | CH$_3$ | CF$_3$ | CH$_3$ |
| F | —N(SO$_2$CH$_3$)$_2$ | CH$_3$ | CF$_3$ | C$_2$H$_5$ |
| F | —N(SO$_2$C$_2$H$_5$)$_2$ | CH$_3$ | CF$_3$ | CH$_3$ |
| F | —N(SO$_2$CH$_3$)$_2$ | Cl | CF$_3$ | CH$_3$ |
| F | —N(SO$_2$CH$_3$)$_2$ | Cl | CF$_3$ | C$_2$H$_5$ |
| F | —N(SO$_2$CH$_3$)(SO$_2$C$_2$H$_5$) | Cl | CF$_3$ | CH$_3$ |
| F | —N(SO$_2$C$_2$H$_5$)$_2$ | Cl | CF$_3$ | CH$_3$ |
| F | —N(SO$_2$CH$_3$)(COOCH$_3$) | H | CF$_3$ | CH$_3$ |

TABLE 1-continued

Examples of the compounds of the formula (IA)

| R¹ | R² | R³ | R⁴ | R⁵ |
|---|---|---|---|---|
| F | —N(SO$_2$CH$_3$)(COOC$_2$H$_5$) | H | CF$_3$ | CH$_3$ |
| F | —N(SO$_2$CH$_3$)(COOC$_4$H$_9$-t) | H | CF$_3$ | CH$_3$ |
| F | —N(SO$_2$CH$_3$)(COOC$_6$H$_5$) | H | CF$_3$ | CH$_3$ |
| F | —N(SO$_2$CH$_3$)(COCH$_3$) | H | CF$_3$ | CH$_3$ |
| F | —N(SO$_2$CH$_3$)(COCF$_3$) | H | CF$_3$ | CH$_3$ |
| F | —N(SO$_2$CH$_3$)(CHO) | H | CF$_3$ | CH$_3$ |
| H | 1-(pyrrolidinyl-SO$_2$)- (5-membered N—SO$_2$ ring) | H | CF$_3$ | CH$_3$ |
| H | 1-(pyrrolidinyl-SO$_2$)- | H | CF$_3$ | C$_2$H$_5$ |
| H | 1-(pyrrolidinyl-SO$_2$)- | CH$_3$ | CF$_3$ | CHF$_2$ |
| F | 1-(pyrrolidinyl-SO$_2$)- | H | CF$_3$ | CH$_3$ |
| F | 1-(pyrrolidinyl-SO$_2$)- | H | CF$_3$ | C$_2$H$_5$ |
| F | 1-(pyrrolidinyl-SO$_2$)- | CH$_3$ | CF$_3$ | CHF$_2$ |
| F | 1-(pyrrolidinyl-SO$_2$)- | Cl | CF$_3$ | CH$_3$ |
| H | 1-(piperidinyl-SO$_2$)- (6-membered N—SO$_2$ ring) | H | CF$_3$ | CH$_3$ |
| H | 1-(piperidinyl-SO$_2$)- | H | CF$_3$ | C$_2$H$_5$ |
| H | 1-(piperidinyl-SO$_2$)- | H | CF$_3$ | CHF$_2$ |
| F | 1-(piperidinyl-SO$_2$)- | H | CF$_3$ | CH$_3$ |
| F | 1-(piperidinyl-SO$_2$)- | H | CF$_3$ | C$_2$H$_5$ |
| F | 1-(piperidinyl-SO$_2$)- | H | CF$_3$ | CHF$_2$ |
| F | 1-(piperidinyl-SO$_2$)- | CH$_3$ | CF$_3$ | CH$_3$ |
| F | 1-(piperidinyl-SO$_2$)- | Cl | CF$_3$ | CH$_3$ |
| H | NHSO$_2$CH=CH$_2$ | H | CF$_3$ | CH$_3$ |
| F | NHSO$_2$CH=CH$_2$ | H | CF$_3$ | CH$_3$ |
| H | NHSO$_2$CH=CH$_2$ | H | CF$_3$ | C$_2$H$_5$ |
| F | NHSO$_2$CH=CH$_2$ | H | CF$_3$ | C$_2$H$_5$ |
| H | NHSO$_2$CH=CH$_2$ | Cl | CF$_3$ | CH$_3$ |
| F | NHSO$_2$CH=CH$_2$ | CH$_3$ | CF$_3$ | CHF$_2$ |
| H | NHSO$_2$N(CH$_3$)$_2$ | H | CF$_3$ | CH$_3$ |
| F | NHSO$_2$N(CH$_3$)$_2$ | H | CF$_3$ | CH$_3$ |
| H | NHSO$_2$N(CH$_3$)$_2$ | H | CF$_3$ | C$_2$H$_5$ |
| F | NHSO$_2$N(CH$_3$)$_2$ | H | CF$_3$ | C$_2$H$_5$ |
| H | NHSO$_2$N(CH$_3$)$_2$ | Cl | CF$_3$ | CH$_3$ |
| F | NHSO$_2$N(CH$_3$)$_2$ | CH$_3$ | CF$_3$ | CH$_3$ |

If, for example, methyl 3-aminocrotonate and 4-cyano-2,5-difluoro-phenyl isothio-cyanate are used as starting materials, the course of the reaction in the process (a) of the invention can be outlined by the following formula scheme:

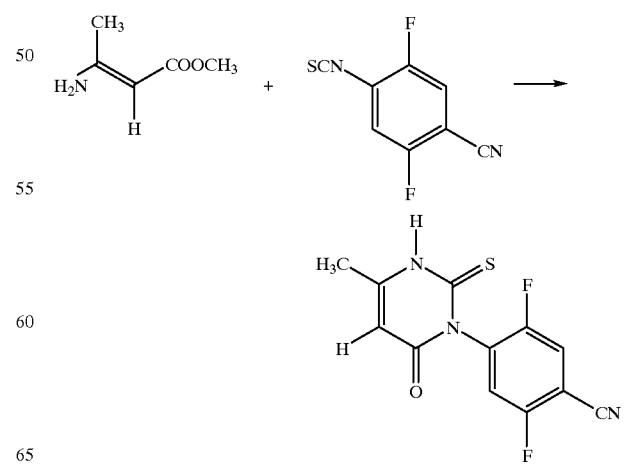

If, for example, 1-(3-chloro-4-cyano-phenyl)-3,6-dihydro-6-oxo-2-thioxo-4-trifluoro-methyl-1(2H)-pyrimidine and methyl bromide are used as starting materials, the course of the reaction in the process (b) of the invention can be outlined by the following formula scheme:

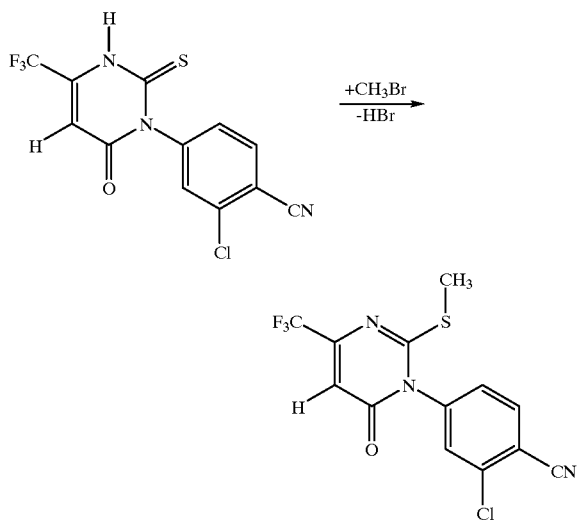

If, for example, 1-(4-cyano-2,5-difluoro-phenyl)-3,6-dihydro-3,4-dimethyl-2-oxo-6-thioxo-1(2H)-pyrimidine and ethanesulphonamide are used as starting materials, the course of the reaction in the process (c) of the invention can be outlined by the following formula scheme:

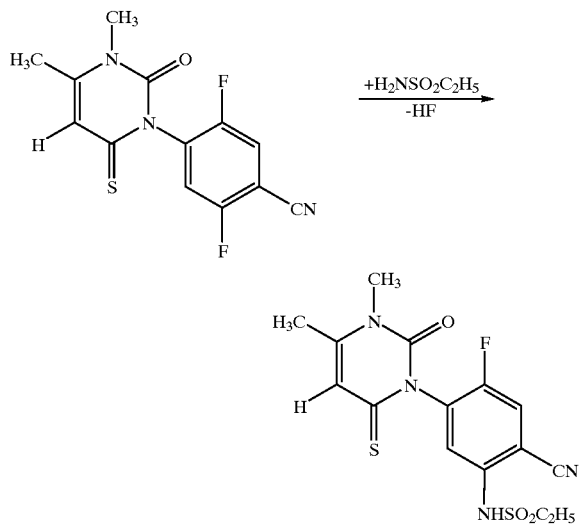

The aminoalkenoic (thio)esters to be used as starting materials for the preparation of compounds of the formula (I) in the process (a) of the invention are generally defined by the formula (II).

In formula (II), $Q^1$, $R^3$ and $R^4$ preferably or in particular have that meaning which has already been given above in connection with the description of the compounds of the invention of the formula (I) as preferred or preferred in particular for $Q^1$, $R^3$ and $R^4$;

R preferably represents $C_1$–$C_4$-alkyl, in particular methyl or ethyl.

The starting materials of the formula (II) are known and/or can be prepared by known processes (cf J. Heterocycl. Chem. 9 (1972), 513–522).

The cyanoaryl iso(thio)cyanates further to be used as starting materials in the process (a) of the invention are generally defined by the formula (III).

In formula (III), $Q^2$, $R^1$ and $R^2$ preferably or in particular have those meanings which have already been given above in connection with the description of the compounds of the invention of the formula (I) as preferred or preferred in particular for $Q^2$, $R^1$ and $R^2$.

The starting materials of the formula (III) are known and/or can be prepared by known processes (cf. J. Org. Chem. 30 (1965), 2465–2466; cf. also DE-P 4327743 and DE-P 4335438).

The cyanoaryl iso(thio)cyanates of the formula (III) are obtained if corresponding cyanoarylamines of the general formula (VII)

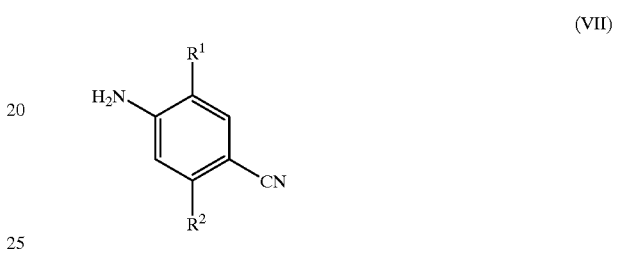

in which $R^1$ and $R^2$ have the meaning given above, are reacted with phosgene or thiophosgene, in the presence or absence of a reaction auxiliary, such as calcium carbonate, and in the presence or absence of diluents, such as methylene chloride, toluene, chlorobenzene and, if appropriate, water, at temperatures between 0° C. and 150° C. (cf. the preparation examples).

The process (a) of the invention for the preparation of the novel compounds of the formula (I) is preferably carried out using diluents. The diluents which are suitable here are virtually all inert organic solvents. These preferably include aliphatic and aromatic, nonhalogenated or halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichloro-benzene, ethers, such as diethyl ether and dibutyl ether, glycol dimethyl ether and di-glycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as acetonitrile and propionitrile, amides such as dimethylformamide, dimethylacetamide and N-methylpyrrolidone and dimethyl sulphoxide, tetramethylene sulphone and hexamethylphosphoric triamide.

The process (a) of the invention is preferably carried out in the presence of a reaction auxiliary. Reaction auxiliaries which are suitable here are principally acid acceptors. Preferably, those which are used are alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates and hydrogen carbonates and alkaline earth metal carbonates and hydrogen carbonates, such as sodium carbonate or hydrogen carbonate and potassium carbonate or hydrogen carbonate and calcium carbonate, alkali metal acetates, such as sodium acetate and potassium acetate, alkali metal alkoxides, such as sodium methoxide, ethoxide, propoxide, isopropoxide, butoxide, isobutoxide and tert-butoxide and potassium methoxide, ethoxide, propoxide, isopropoxide, butoxide, isobutoxide and tert-butoxide, in addition basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures can be varied in a relatively wide range in the process (a) of the invention. Generally, temperatures between −120° C. and +100° C. are employed, preferably temperatures between −70° C. and +80° C.

The process (a) of the invention is generally carried out at atmospheric pressure. However, it is also possible to employ elevated or reduced pressure.

To carry out the process (a) of the invention, the starting materials needed in each case are generally used in approximately equimolar amounts. However, it is also possible to employ one of the two components used in each case in a relatively great excess. The reactions are generally carried out in a suitable diluent in the presence of a reaction auxiliary, and the reaction mixture is stirred for a plurality of hours at the temperature required in each case. The workup in the process (a) of the invention is performed in each case by conventional methods (cf. the preparation examples).

The N-cyanoaryl nitrogen heterocycles to be used as starting materials for the preparation of compounds of the formula (I) in the process (b) of the invention are generally defined by the formulae (IA) and (IB)—with the proviso that $R^5$ represents hydrogen therein.

In the formulae (IA) and (IB), $Q^1$, $Q^2$, $R^1$, $R^2$, $R^3$ and $R^4$ preferably or in particular have those meanings which have already been given above in connection with the description of the compounds of the invention of the formula (I) as preferred or preferred in particular for $Q^1$, $Q^2$, $R^1$, $R^2$, $R^3$ and $R^4$.

The starting materials of the formulae (IA) and (B) for process (b) are novel compounds of the invention, they can be prepared by the process (a) of the invention.

The alkylating agents further to be used as starting materials in the process (b) of the invention are generally defined by the formulae (IV) and (V).

In the formulae (IV) and (V), $R^5$ preferably or in particular has that meaning which has already been given above in connection with the description of the compounds of the invention of the formula (I) as preferred or preferred in particular for $R^5$.

The starting materials of the formulae (IV) and (V) are known organic synthesis chemicals.

The process (b) of the invention is preferably carried out using a diluent. Those diluents are suitable here, principally, which have already been mentioned in the description of the process (a) of the invention.

Acid acceptors which can be used in the process (b) of the invention are all acid binders which are conventionally usable for such reactions. Preferably, those which can be used are alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates and hydrogen carbonates and alkaline earth metal carbonates and hydrogen carbonates, such as sodium carbonate or hydrogen carbonate and potassium carbonate or hydrogen carbonate and calcium carbonate, alkali metal acetates, such as sodium acetate and potassium acetate, alkali metal alkoxides, such as sodium methoxide, ethoxide, propoxide, isopropoxide, butoxide, isobutoxide and tert-butoxide and potassium methoxide, ethoxide, propoxide, isopropoxide, butoxide, isobutoxide and tert-butoxide, in addition basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures in the process (b) of the invention can be varied within a relatively wide range. Generally, temperatures between 0° C. and 120° C. are employed, preferably temperatures between 10° C. and 100° C.

The process (b) of the invention is generally carried out at atmospheric pressure. However, it is also possible to employ elevated or reduced pressure.

To carry out the process (b) of the invention, the starting materials needed in each case are generally used in approximately equimolar amounts. However, it is also possible to employ one of the two components used in each case in a relatively great excess. The reactions are generally carried out in a suitable diluent in the presence of an acid acceptor, and the reaction mixture is stirred for a plurality of hours at the temperature required in each case. The workup in the process (b) of the invention is carried out in each case by conventional methods (cf. the preparation examples).

The N-cyanoaryl nitrogen heterocycles to be used as starting materials for the preparation of compounds of the formula (I) in the process (c) of the invention are generally defined by the formula (I)—with the proviso that $R^2$ represents halogen therein.

In formula (I), $Q^1$, $Q^2$, $R^1$, $R^3$, $R^4$ and Z preferably or in particular then have those meanings which have already been given above as preferred or as preferred in particular for $Q^1$, $Q^2$, $R^1$, $R^3$, $R^4$ and Z in connection with the description of the compounds of the formula (I) of the invention.

The starting materials of the formula (I) for process (c) are novel compounds of the invention; they can be prepared by the processes (a) and (b) of the invention.

The amides further to be used as starting materials in the process (c) of the invention are generally defined by the formula (VI).

In formula (VI), A and $A^1$ preferably or in particular have that meaning which has already been given above as preferred or preferred in particular for A and $A^1$ in connection with the description of the compounds of the formula (I) of the invention.

The starting materials of the formula (VI) are known organic synthesis chemicals.

The process (c) of the invention is preferably carried out using a diluent. Those diluents which are suitable here are principally those which have already been mentioned in the description of the process (a) of the invention.

The process (c) of the invention is carried out in the presence or absence of an acid acceptor. Those acid acceptors are suitable here which have already been mentioned in the description of the process (b) of the invention.

The reaction temperatures in the process (c) of the invention can be varied in a relatively broad range. Generally, temperatures between 0° C. and 200° C. are employed, preferably temperatures between 20° C. and 180° C.

The process (c) of the invention is generally carried out at atmospheric pressure. However, it is also possible to employ elevated or reduced pressure.

To carry out the process (c) of the invention, the starting materials required in each case are generally used in approximately equimolar amounts. However, it is also possible to employ one of two components used in each case in a relatively great excess. The reactions are generally carried out in a suitable diluent in the presence of an acid acceptor, and the reaction mixture is stirred for a plurality of hours at the temperature required in each case. The workup in the process (c) of the invention is performed in each case by conventional methods (cf. the preparation examples).

The active compounds of the invention can be used as defoliants, desiccants, herbicides and, in particular, as weed killers. Weeds in the broadest sense are taken to mean all plants which grow at places where they are not desired. Whether the substances of the invention act as total or selective herbicides essentially depends on the application rate.

The active compounds of the invention can be used, eg., in the case of the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Panunculus and Taraxacum.

Dicotyledonous cultivated plants of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous cultivated plants of the genera: Oryza, Zea, Triticum, Hordeum, Avena, Secale, Sorghum, Panicum, Saccharum, Ananas, Asparagus and Allium.

However, the use of the active compounds of the invention is in no way restricted to these genera, but also extends in a similar manner to other plants.

The compounds, depending on the concentration, are suitable for total weed control, eg. on industrial areas and railway tracks and on paths and grounds with or without tree growth. Likewise, the compounds can be used for weed control in permanent cultivation, eg. forest, ornamental wood plantations, fruit cultivation, vineyards, citrus plantations, nut plantations, banana plantations, coffee plantations, tea plantations, rubber plantations, oil palm plantations, cocoa plantations, berry fruit plantations and hopfields, on ornamental lawns and sports fields and grazing areas and for selective weed control in annual cultivations.

The compounds of the formula (I) of the invention are suitable, in particular, for the selective control of monocotyledonous and dicotyledonous weeds in monocotyledonous and dicotyledonous cultivations both in the preemergence and postemergence methods.

The active compounds are also suitable for controlling animal pests, preferably arthropods and nematodes, in particular insects and arachnids, which occur in agriculture, in forestry, in the protection of stored products and materials and in the hygiene sector. They are active against species of usual sensitivity and resistance and against all or individual development stages. The pests mentioned above include:

From the order of the Isopoda, eg. *Oniscus asellus, Armadillidium vulgare* and *Porcellio scaber.*

From the order of the Diplopoda, eg. *Blaniulus guttulatus.*

From the order of the Chilopoda, eg. *Geophilus carpophagus* and Scutigera spec.

From the order of the Symphyla, eg. *Scutigerella immaculata.*

From the order of the Thysanura, eg. *Lepisma saccharina.*

From the order of the Collembola, eg. *Onychiurus armatus.*

From the order of the Orthoptera, eg. *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, eg. *Forficula auricularia.*

From the order of the Isoptera, eg. Reticulitermes spp.

From the order of the Anoplura, eg. *Phylloxera vastatrix,* Pemphigus spp., *Pediculus humanus corporis,* Haematopinus spp. and Linognathus spp.

From the order of the Mallophaga, eg. Trichodectes spp. and Damalinea spp.

From the order of the Thysanoptera, eg. *Hercinothrips femoralis* and *Thrips tabaci.*

From the order of the Heteroptera, eg. Eurygaster spp., *Dysdercus intermedius, Piesma quadrata, Cimex lectularius, Rhodnius prolixus* and Triatoma spp.

From the order of the Homoptera, eg. *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, eg. *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Caprocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, eg. *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp.,

*Tenebrio molitor,* Agriotes spp., Conoderus spp., *Melolontha melolontha, Amphimallon solstitialis* and *Costelytra zealandica.*

From the order of the Hymenoptera, eg. Diprion spp., Hoplocampa spp., Lasius spp., *Monomorium pharaonis* and Vespa spp.

From the order of the Diptera, eg. Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, eg. *Xenopsylla cheopis* and Ceratophyllus spp.

From the order of the Arachnida, eg. *Scorpio maurus* and *Latrodectus mactans.*

From the order of the Acarina, eg. *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytopathogenic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The active compounds can be converted into the conventional formulations, such as solutions, emulsions, wettable powders, suspensions, powders, dusts, pastes, soluble powders, granules, suspension/emulsion concentrates, natural and synthetic materials impregnated with active compound and very fine encapsulations in polymeric materials.

These formulations are prepared in a known manner, eg. by mixing the active compounds with extenders, that is liquid solvents and/or solid carriers, with or without the use of surfactants, that is emulsifiers and/or dispersants and/or foam-forming agents.

In the case of the use of water as extender, eg. organic solvents can also be used as solubilizer. Liquid solvents which are suitable are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, eg. mineral oil fractions, mineral and vegetable oils, alcohols such as butanol or glycol and their ethers and esters, ketones such as acetone, methyl ethyl ketone, methyl isobutyl ketone or cyclohexanone, highly polar solvents, such as dimethylformamide and dimethyl sulphoxide, and water.

Solid carriers which are useful are:

eg. ammonium salts and natural rock flours, such as kaolins, clays, talcum, chalk, quartz, attapulgite, montmorillonite or diatomaceous earth and synthetic rock flours, such as highly disperse silica, aluminium oxide and silicates; solid carriers for granules which are suitable are: eg. crushed and fractionated natural rocks such as calcite, marble, pumice, sepiolite, dolomite and synthetic granules of inorganic and organic flours and granules from organic material such as sawdust, coconut shells, corn cobs and tobacco stalks; emulsifiers and/or foam-forming agents which are suitable are: eg. nonionogenic and anionic emulsifiers, such as polyoxyethylene fatty acid esters, polyoxythylene fatty alcohol ethers, eg. alkylaryl polyglycol ethers, alkylsulphonates, alkyl-sulphates, arylsulphonates and protein hydrolysates; dispersants which are suitable are: eg. lignin sulphite liquors and methylcellulose.

In the formulations, binding agents such as carboxymethylcellulose, natural and synthetic pulverulent, granular or latex-like polymers, can be used, such as gum arabic, poly(vinyl alcohol), poly(vinyl acetate), and natural phospholipids, such as cephalins and lecithins and synthetic phospholipids. Other additives can be mineral and vegetable oils.

Colourants can be used, such as inorganic pigments, eg. iron oxide, titanium oxide, Prussian Blue and organic colourants, such as alizarin, azo and metallophthalocyanine colourants and trace nutrients such as salts of iron, manganese, boron, copper, cobalt, molybdenum and zinc.

The formulations generally contain between 0.1 and 95% by weight of active compound, preferably between 0.5 and 90%.

The active compounds of the invention can also be used as such or in their formulations in a mixture with known herbicides for weed control, ready-to-use formulations or tank mixtures being possible.

Known herbicides are suitable for the mixtures, for example anilides such as diflufenican and propanil; arylcarboxylic acids such as dichloropicolinic acid, dicamba and picloram; aryloxyalkanoic acids such as 2,4 D, 2,4 DB, 2,4 DP, fluroxypyr, MCPA, MCPP and triclopyr; aryloxyphenoxy-alkanoic esters such as diclofop-methyl, fenoxaprop-ethyl, fluazifop-butyl, haloxyfop-methyl and quizalofop-ethyl; azinones such as chloridazon and norflurazon; carbamates such as chlorpropham, desmedipham, phen-medipham and propham; chloroacetanilides such as alachlor, acetochlor, butachlor, metazachlor, metolachlor, pretilachlor and propachlor; dinitroanilines such as oryzalin, pendimethalin and trifluralin; diphenyl ethers such as acifluorfen, bifenox, fluoro-glycofen, fomesafen, halosafen, lactofen and oxyfluorfen; ureas such as chlortoluron, diuron, fluometuron, isoproturon, linuron and methabenzthiazuron; hydroxylamines such as alloxydim, clethodim, cycloxydim, sethoxydim and tralkoxydim; imidazolinones such as imazethapyr, imazamethabenz, imazapyr and imazaquin; nitriles such as bromoxynil, dichlobenil and ioxynil; oxyacetamides such as mefenacet; sulphonylureas such as amidosulfuron, bensulfuron-methyl, chlorimuron-ethyl, chlorsulfuron, cinosulfuron, met-sulfuron-methyl, nicosulfuron, primisulfuron, pyrazosulfuron-ethyl, thifensulfuron-methyl, triasulfuron and tribenuron-methyl; thiolcarbamates such as butylate, cycloate, diallate, EPTC, esprocarb, molinate, prosulfocarb, thiobencarb and triallate; triazines such as atrazine, cyanazine, simazine, simetryne, terbutryne and terbuthylazine; triazinones such as hexazinone, metamitron and metribuzin; others such as aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinclorac, quinmerac, sulphosate and tridiphane.

A mixture with other known active compounds, such as fungicides, insecticides, acaricides, nematicides, bird repellants, plant nutrients and soil structure improvers is also possible.

The active compounds can be applied as such, in the form of their formulations or the application forms prepared therefrom by further dilution, such as ready-to-use solutions, suspensions, emulsions, powders, pastes and granules. They are applied in a conventional manner, eg. by pouring, sprinkling, spraying, scattering.

The active compounds of the invention can be applied either before or after the emergence of plants. They can also be incorporated into the soil before sowing.

The active compound application rate can vary in a relatively broad range. It essentially depends on the type of effect desired. Generally, the application rates are between 10 g and 10 kg of active compound per hectare of soil surface, preferably between 50 g and 5 kg per ha.

The preparation and use of the active compounds of the invention follow from the examples below.

PREPARATION EXAMPLES

Example 1

(Process (a))

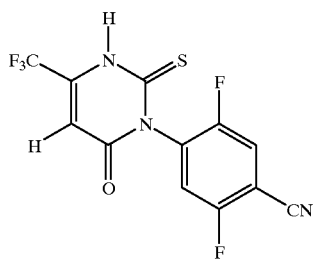

1.8 g (10 mmol) of ethyl 3-amino-4,4,4-trifluoro-crotonate are introduced into 30 ml of dimethylformamide and 2 ml of toluene and 0.4 g (10 mmol) of sodium hydride (80% strength) are added at 0° C. to +5° C. The mixture is stirred at the temperature specified for 30 minutes. After cooling to −70° C., 1.0 g (5 mmol) of 4-cyano-2,5-difluoro-phenyl isothiocyanate are added and the reaction mixture is stirred for 2 hours at −70° C., then for a further 15 hours at +20° C. and finally for 4 hours at +50° C. 2 ml of acetic acid are then added to the mixture, it is diluted with water to about twice the volume and extracted with ethyl acetate. The organic phase is concentrated and the crude product remaining as residue is purified by column chromatography (silica gel; initial run with methylene chloride discarded; main fraction with ethyl acetate). The main fraction eluted is concentrated and the residue is brought to crystallization by digestion with diethyl ether.

0.3 g (9% of theory) of 1-(4-cyano-2,5-difluoro-phenyl)-3,6-dihydro-2-thioxo-6-oxo-4-trifluoromethyl-1(2H)-pyrimidine are obtained of melting point 187° C.

Example 2

(Process (b))

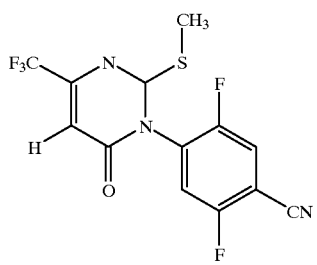

0.9 g (2.7 mmol) of 1-(4-cyano-2,5-difluoro-phenyl)-3,6-dihydro-2-thioxo-6-oxo-4-trifluoromethyl-1(2H)-pyrimidine and 0.37 g (2.7 mmol) of potassium carbonate are introduced into 10 ml of acetone and 0.38 g (2.7 mmol) of methyl iodide is added at −10° C. The reaction mixture is stirred for 15 hours at +20° C. and then filtered. The solvent is carefully distilled off from the filtrate in a water-jet vacuum.

1.0 g (approximately 100% of theory) of 1-(4-cyano-2,5-difluoro-phenyl)-1,6-dihydro-2-methylthio-6-oxo-4-trifluoromethyl-pyrimidine are obtained as oily residue.

$^1$H-NMR (dimethyl sulphoxide $D_6$, δ): 7.02 ppm.

Example 3

(Process (a))

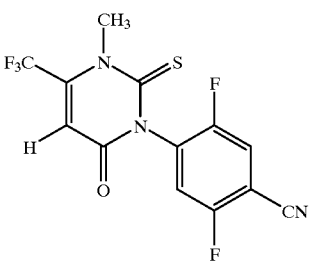

9.9 g (50 mmol) of ethyl 3-methylamino-4,4,4-trifluoro-crotonate are introduced into 100 ml of dimethylformamide and 10 ml of toluene and 2.0 g (50 mmol) of sodium hydride (60% strength) are added at −15° C. The mixture is stirred at the temperature specified for 15 minutes, then 5.0 g (25 mmol) of 4-cyano-2,5-difluorophenyl isothiocyanate are added and the mixture is stirred for 15 hours at 20° C.

6 ml of acetic acid are then added; the mixture is diluted to about twice the volume with water and extracted with ethyl acetate. The organic phase is concentrated and the crude product remaining as residue is purified by column chromatography (silica gel; methylene chloride). The main fraction eluted is concentrated and the residue is brought to crystallization by digestion with diisopropyl ether.

1.1 g (13% of theory) of 1-(4-cyano-2,5-difluoro-phenyl)-3,6-dihydro-2-thioxo-6-oxo-3-methyl-4-trifluoromethyl-1(2H)-pyrimidine are obtained of melting point 191° C.

Example 4

(Process (a))

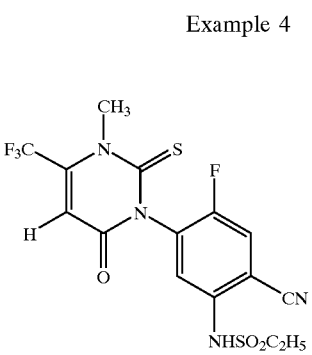

2.1 g (10.5 mmol) of ethyl 3-methylamino-4,4,4-trifluorocrotonate are introduced into 50 ml of dimethylformamide and 5 ml of toluene and 0.4 g (10.9 mmol) of sodium hydride (60% strength) is added at −70° C. The mixture is stirred at the temperature specified for 15 minutes and then 2.0 g (7 mmol) of 4-cyano-2-fluoro-5-ethylsulphonylamino-phenyl isothiocyanate are added. The reaction mixture is then stirred for 4 hours at −60° C., and 6 ml of acetic acid are then added and the mixture is diluted with water to about twice the volume. The organic phase is separated off and concentrated. The residue is brought to crystallization by digestion with diisopropyl ether.

0.7 g (25% of theory) of 1-(4-cyano-2-fluoro-5-ethylsulphonylamino-phenyl)-3,6-dihydro-2-thio-6-oxo-3-methyl-4-trifluoromethyl-1(2H)-pyrimidine is obtained of melting point 150° C.

Analogously to the Examples 1 to 4 and in accordance with the general description of the preparation methods of the invention, the compounds of the formula (I)—or of the formula (IA) or (IB)—listed in Table 2 below can also be prepared, for example.

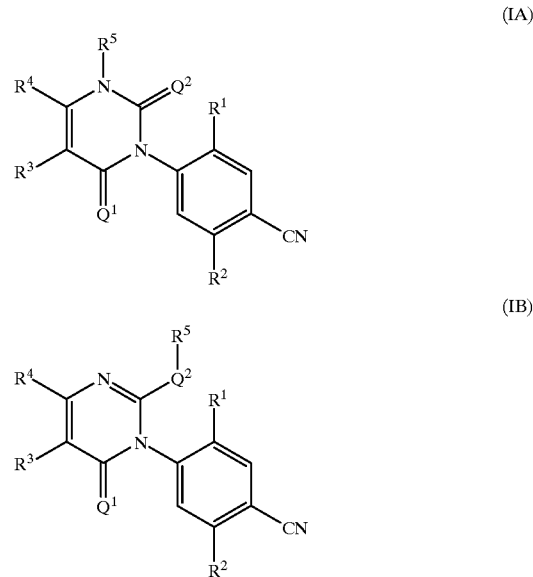

(IA)

(IB)

TABLE 2

Examples of the compounds of the formula (I)

| Ex. No. | General formula | $Q^1$ | $Q^2$ | $R^1$ | $R^2$ | $R^3$ | $R^4$ | $R^5$ | Melting point (° C.) |
|---|---|---|---|---|---|---|---|---|---|
| 5 | IA | O | S | F | —NHSO$_2$C$_3$H$_7$ | H | CF$_3$ | CH$_3$ | 162 |
| 6 | IA | O | S | F | —NHSO$_2$CH$_3$ | H | CF$_3$ | H | |
| 7 | IB | O | S | F | —NHSO$_2$CH$_3$ | H | CF$_3$ | CH$_3$ | |
| 8 | IA | O | S | F | —NHSO$_2$CH$_3$ | H | CF$_3$ | CH$_3$ | 214 |
| 9 | IB | O | S | F | —N(CH$_3$)SO$_2$CH$_3$ | H | CF$_3$ | CH$_3$ | |
| 10 | IB | O | S | F | —NHSO$_2$C$_2$H$_5$ | H | CF$_3$ | CH$_3$ | |
| 11 | IB | O | S | F | —NHSO$_2$CH$_3$ | H | CF$_3$ | C$_2$H$_5$ | |
| 12 | IB | O | S | F | —NHSO$_2$C$_2$H$_5$ | H | CF$_3$ | C$_3$H$_7$ | |
| 13 | IB | O | S | F | —NHSO$_2$C$_3$H$_7$ | H | CF$_3$ | CHF$_2$ | |
| 14 | IB | O | S | F | —NHSO$_2$CH(CH$_3$)$_2$ | H | CF$_3$ | CH$_3$ | |
| 15 | IA | O | S | F | —NHSO$_2$CH(CH$_3$)$_2$ | H | CF$_3$ | CH$_3$ | 114 |
| 16 | IA | O | S | F | —NHSO$_2$CH$_3$ | H | CF$_3$ | C$_2$H$_5$ | |
| 17 | IA | O | S | F | —NHSO$_2$CH$_3$ | H | CF$_3$ | C$_3$H$_7$ | |
| 18 | IA | O | S | F | —NHSO$_2$C$_2$H$_5$ | H | CF$_3$ | CHF$_2$ | |
| 19 | IA | O | S | F | —N(C$_2$H$_5$)SO$_2$CH$_3$ | H | CF$_3$ | CH$_3$ | |
| 20 | IA | O | S | F | —NHSO$_2$-cyclopropyl | H | CF$_3$ | CH$_3$ | 208 |
| 21 | IA | O | S | F | —NHSO$_2$C$_4$H$_9$ | H | CF$_3$ | CH$_3$ | 161 |
| 22 | IA | O | S | F | —NHSO$_2$-phenyl | H | CF$_3$ | CH$_3$ | |
| 23 | IA | O | S | F | —NHSO$_2$CH$_3$ | H | CHF$_2$ | CH$_3$ | |

TABLE 2-continued

Examples of the compounds of the formula (I)

| Ex. No. | General formula | $Q^1$ | $Q^2$ | $R^1$ | $R^2$ | $R^3$ | $R^4$ | $R^5$ | Melting point (° C.) |
|---|---|---|---|---|---|---|---|---|---|
| 24 | IA | O | S | F | —NHSO$_2$CH$_3$ | H | CF$_2$Cl | CH$_3$ | |
| 25 | IA | O | S | F | —NHSO$_2$C$_2$H$_5$ | H | CF$_2$Cl | CH$_3$ | |
| 26 | IA | O | S | F | —NHSO$_2$C$_2$H$_5$ | H | CF$_3$ | C$_2$H$_5$ | |
| 27 | IA | O | S | H | —NHSO$_2$CH$_3$ | H | CF$_3$ | CH$_3$ | |
| 28 | IA | O | S | H | —NHSO$_2$C$_2$H$_5$ | H | CF$_3$ | CH$_3$ | |
| 29 | IA | O | S | Cl | —NHSO$_2$CH$_3$ | H | CF$_3$ | ▷— | |
| 30 | IA | O | S | Cl | —NHSO$_2$C$_3$H$_7$ | H | CF$_3$ | CH$_3$ | |
| 31 | IA | O | S | F | —NHSO$_2$C$_2$H$_5$ | H | CF$_3$ | C$_2$H$_5$ | 177 |
| 32 | IA | O | S | F | —N(SO$_2$CH$_3$)(SO$_2$C$_2$H$_5$) | H | CF$_3$ | CH$_3$ | 122 |
| 33 | IA | O | S | F | —N(CH$_3$)SO$_2$C$_2$H$_5$ | H | CF$_3$ | CH$_3$ | 68 |
| 34 | IA | O | S | F | —N(CH$_3$)SO$_2$CH$_3$ | H | CF$_3$ | CH$_3$ | |
| 35 | IA | O | S | F | —NHSO$_2$CH$_3$ | H | CHF$_2$ | CH$_3$ | 220 |

The compound listed in Table 2 as Example 32 can be prepared, for example, as follows:

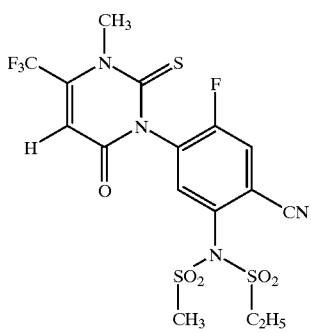

A mixture of 2.0 g (4.4 mmol) of 1-(4-cyano-2-fluoro-5-ethylsulphonylamino-phenyl)-3,6-dihydro-2-thio-6-oxo-3-methyl-4-trifluoromethyl- 1(2H)-pyrimidine, 0.64 g (5.6 mmol) of methanesulphonyl chloride, 0.8 g (8 mmol) of triethylamine and 50 ml of acetonitrile is stirred for 15 hours at 20° C. and then the mixture is concentrated in a water-jet vacuum. The residue is stirred with water and the product produced in the crystalline state is isolated by filtration.

2.3 g (100% of theory) of 1-(4-cyano-2-fluoro-5-(N-ethylsulphonyl-N-methylsulphonyl-amino)-phenyl)-3,6-dihydro-2-thio-6-oxo-3-methyl-4-trifluoromethyl-1(2H)-pyrimidine are obtained of melting point 122° C.

The compound listed in Table 2 as Example 33 can be prepared, for example, as follows:

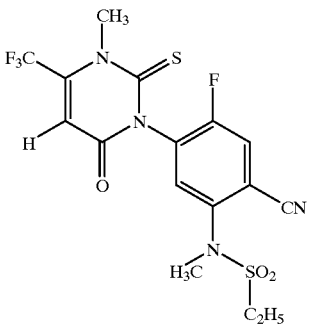

A mixture of 1.5 g (3.4 mmol) of 1-(4-cyano-2-fluoro-5-ethylsulphonylamino-phenyl)-3,6-dihydro-2-thio-6-oxo-3-methyl-4-trifluoromethyl-1(2H)-pyrimidine, 0.5 g (3.8 mmol) of potassium carbonate and 30 ml of acetonitrile is stirred for 30 minutes at 20° C. and then 0.5 g (3.8 mmol) of dimethyl sulphate is added. The reaction mixture is then refluxed for 5 hours and stirred for a further 60 hours at 20° C. The mixture is then concentrated in a water-jet vacuum, the residue is stirred with water and the product produced in the crystalline state is isolated by filtration.

1.2 g (78% of theory) of 1-(4-cyano-2-fluoro-5-(N-ethylsulphonyl-N-methyl-amino)-phenyl)-3,6-dihydro-2-thio-6-oxo-3-methyl-4-trifluoromethyl-1(2H)-pyrimidine are obtained of melting point 68° C.

Starting Materials of the Formula (III)

Example (III-1)

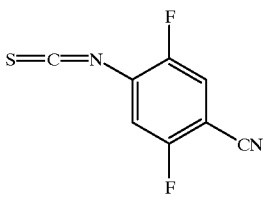

10.0 g (65 mmol) of 4-cyano-2,5-difluoro-aniline are introduced into 100 ml of toluene and 8.2 g (71 mmol) of thiophosgene are slowly added to the mixture heated to 80° C. to 90° C. The reaction mixture is then refluxed for approximately 40 hours. Then, after the solvent has been carefully distilled off under reduced pressure, the product (4-cyano-2,5-difluoro-phenyl isothiocyanate) is obtained as an ochre colourant.

$^1$H-NMR (CDCl$_3$, δ): 7.03 ppm.

Application Examples

Example A
Pre-emergence Test

| Solvent: | 5 parts by weight of acetone |
|---|---|
| Emulsifier: | 1 part by weight of alkylaryl polyglycol ether |

To prepare an expedient active compound preparation, 1 part by weight of active compound is mixed with the specified amount of solvent, the specified amount of emulsifier is added and the concentrate is diluted with water to the desired concentration.

Seeds of the test plants are sown in standard soil and are watered after 24 hours with the active compound preparation. The amount of water per unit area is expediently kept constant during this. The active compound concentration in the preparation is not important, only the application rate of the active compound per unit area is critical. After three weeks, the degree of damage of the plants is evaluated in % damage in comparison with the development of the untreated control. In the evaluation:

0% denotes no effect (as untreated control)
100% denotes total destruction

In this test, the compounds, for example, according to the Preparation Examples 3, 4, 7 and 8 display, with good compatibility with cultivated plants, such as wheat (0%), high activity against weeds such as Abutilon (80–100%), Amaranthus (70–100%), Ambrosia (95–100%), Galinsoga (90–100%), Portulaca (90–100%) and Solanum (80–100%) at an application rate of 60 g per hectare.

Example B
Post-emergence Test

| Solvent: | 5 parts by weight of acetone |
|---|---|
| Emulsifier: | 1 part by weight of alkylaryl polyglycol ether |

To prepare an expedient active compound preparation, 1 part by weight of active compound is mixed with the specified amount of solvent, the specified amount of emulsifier is added and the concentrate is diluted with water to the desired concentration.

Test plants which have a height of 5–15 cm are sprayed with the active compound preparation in such a way that the amounts of active compound per unit area desired in each case are applied. After three weeks, the degree of damage of the plants is evaluated in % damage in comparison with the development of the untreated control.

In the evaluation:
0% denotes no effect (as untreated control)
100% denotes total destruction In this test, the compounds, for example, according to the Preparation Examples 3, 4 and 8 display, with very good compatibility with cultivated plants, such as wheat (5%), without exception, high activity against weeds such as Abutilon (100%), Chenopodium (100%), Ipomoea (100%), Solanum (100%) and Veronica (100%), at an application rate of only 30 g per hectare.

Example C
Phaedon Larvae Test

Solvent: 7 parts by weight of dimethylformamide
Emulsifier: 1 part by weight of alkylaryl polyglycol ether To produce an expedient active compound preparation, 1 part by weight of active compound is mixed with the specified amount of solvent and the specified amount of emulsifier and the concentrate is diluted with water to the desired concentration.

Cabbage leaves (*Brassica oleracea*) are treated by dipping them into the active compound preparation of the desired concentration and populated with horseradish leaf beetle larvae *Phaedon cochleariae,* as long as the leaves are still moist.

After the desired time, the destruction is determined in %. In the determination, 100% denotes that all beetle larvae have been destroyed; 0% denotes that no beetle larvae have been destroyed.

In this test the compound, for example, according to Preparation Example 3 displays a degree of destruction of 100% after 3 days at an active compound concentration of 0.1%.

What is claimed is:

1. A compound of the formula (I)

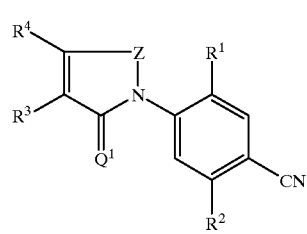

wherein
Q$^1$ represents oxygen or sulphur,
R$^1$ represents hydrogen, fluorine, chlorine or bromine,
R$^2$ represents fluorine, chlorine, bromine, cyano, nitro, unino or the grouping —N(A$^1$)SO$_2$A, in which
  A represents a radical selected from the group consisting of alkyl alkenyl, alkinyl or dialkylamino each having up to 10 carbon atoms and each of which is optionally substituted by fluorine, chlorine, bromine, cyano or C$_1$–C$_4$-alkoxy,
  A further represents cycloalkyl or cycloalkylalkyl each of which is optionally substituted by fluorine, chlorine, bromine, cyano or C$_1$–C$_4$-alkyl, having 3 to 8 carbon atoms in the cycloalkyl moiety and, when present, 1 to 4 carbon atoms in the alkyl portion of the cycloalkylalkyl moiety, A further represents aryl or arylalkyl, each of which is optionally substituted by fluorine, chlorine, bromine, cyano, nitro, carboxy, carbamoyl, by $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl (which are each optionally substituted by fluorine and/or chlorine), by dimethylaminosulphonyl or diethylaminosulphonyl, by $C_1$–$C_4$-alkoxy-carbonyl (which is optionally substituted by fluorine, chlorine, bromine, methoxy or ethoxy), by, phenyl or phenyloxy (which are each optionally substituted by fluorine, chlorine, bromine, cyano, methyl, methoxy, trifluoromethyl and/or trifluoromethoxy), having 6 or 10 carbon atoms in the aryl moiety and, 1 to 4 carbon atoms in the alkyl portion of the cycloalkylalkyl moiety, and $A^1$ represents hydrogen or formyl, or $C_1$–$C_4$-alkyl which is optionally substituted by fluorine and/or chlorine, cyano or $C_1$–$C_4$-alkoxy-carbonyl, or $C_1$–$C_4$-alkyl-carbonyl or $C_1$–$C_4$-alkoxy-carbonyl, each of which is optionally substituted by fluorine, chlorine or $C_1$–$C_4$-alkoxy, or $C_1$–$C_4$-alkylsulphonyl which is optionally substituted by fluorine and/or chlorine, or together with A represents alkanediyl having 2 to 8 carbon atoms, $R^3$ represents hydrogen, fluorine, chlorine, bromine, cyano or alkyl, which is optionally substituted by fluorine and/or chlorine, having 1 to 4 carbon atoms, $R^4$ represents alkyl, which is optionally substituted by fluorine, chlorine, bromine, methoxy or ethoxy, having 1 to 6 carbon atoms, or together with $R^3$ represents alkanediyl having 2 to 8 carbon atoms, and Z represents one of the groupings below

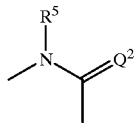 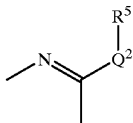

in which $Q^2$ represents oxygen or sulphur and $R^5$ represents hydrogen or alkyl, alkenyl, alkinyl or alkylcarbonyl each of which is optionally substituted by fluorine, chlorine, bromine, cyano, $C_1$–$C_4$-alkoxy, $C_1$–$C_4$-alkyl-carbonyl or $C_1$–$C_4$-alkoxy-carbonyl, and each of which has up to 6 carbon atoms, or a salt thereof, with the proviso that at least one of the groupings $Q^1$ or $Q^2$ represents sulphur.

2. An N-cyanoaryl nitrogen heterocycle according to claim 1, wherein $Q^1$ represents oxygen or sulphur, $R^1$ represents hydrogen, fluorine or chlorine, $R^2$ represents fluorine, chlorine, bromine, cyano, amino or the grouping —N($A^1$)SO$_2$A, in which A represents a radical selected from the group consisting of methyl, ethyl, n- or i-propyl, n-, i-, s- or t-butyl, ethenyl, propenyl, butenyl, each of which is optionally substituted by fluorine or chlorine, or represents dimethylamino, A further represents cyclopropyl, cyclopentyl, cyclohexyl, cyclopropylmethyl, cyclopentylmethyl or cyclohexylmethyl, each of which is optionally substituted by fluorine, chlorine, bromine, methyl and/or ethyl, A further represents phenyl, naphthyl, phenylmethyl or phenylethyl, each of which is optionally substituted by fluorine, chlorine, bromine, cyano, nitro, carboxy, methyl, trifluoromethyl, methoxy, ethoxy, difluoromethoxy, trifluoromethoxy, methylthio, ethylthio, methylsulphinyl, ethylsulphinyl, methylsulphonyl, ethylsulphonyl, dimethylaminosulphonyl, methoxycarbonyl, ethoxycarbonyl, propoxycarbonyl or phenyl, and $A^1$ represents hydrogen, formyl, methyl, ethyl, acetyl, propionyl, methoxycarbonyl, ethoxycarbonyl, methylsulphonyl or ethylsulphonyl, or together with A represents trimethylene or tetramethylene, $R^3$ represents hydrogen, fluorine, chlorine, bromine, methyl, trifluoromethyl, ethyl, n- or i-propyl, $R^4$ represents methyl, ethyl, n- or i-propyl, each of which is optionally substituted by fluorine or chlorine, or together with $R^3$ represents trimethylene or tetramethylene, and Z represents one of the groupings below

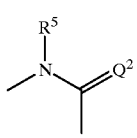 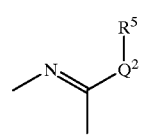

in which $Q^2$ represents oxygen or sulphur and $R^5$ represents hydrogen, methyl, difluoromethyl, cyanomethyl, ethyl, fluoroethyl, chloroethyl, difluoroethyl, dichloroethyl, trifluoroethyl, chlorodifluoroethyl, cyanoethyl, n- or i-propyl, fluoropropyl, chloropropyl, cyanopropyl, allyl, chloroallyl, propargyl, acetyl, propionyl, fluoroacetyl, chloroacetyl, difluoroacetyl, dichloroacetyl, trifluoroacetyl or trichloroacetyl, or a salt thereof.

3. An N-cyanoaryl nitrogen heterocycle according to claim 1, wherein the salt is a sodium salt, a potassium salt, a calcium salt, an ammonium salt, a $C_1$–$C_4$-alkyl-ammonium salt, a di-($C_1$–$C_4$-alkyl)-ammonium salt, a tri-($C_1$–$C_4$-alkyl)-ammonium salt, a cyclopentyl-ammonium salt, or a cyclohexyl-ammonium salt.

4. An N-cyanonitrogen heterocycle according to claim 1 wherein Z is

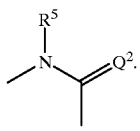

5. An N-cyanonitrogen heterocycle according to claim 1 wherein Z is

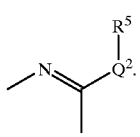

6. An N-cyanonitrogen heterocycle according to claim 5, wherein $Q^1$ represents oxygen and $Q^2$ represents sulphur.

7. An N-cyanonitrogen heterocycle according to claim 1, wherein $Q^1$ represents oxygen and $Q^2$ represents sulphur.

8. An N-cyanonitrogen heterocycle according to claim 1, wherein the compound is

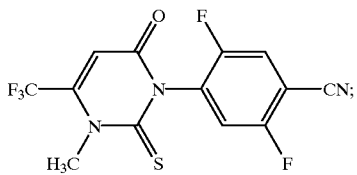

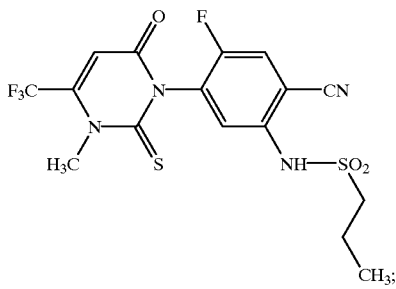

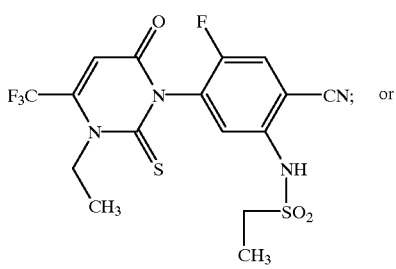 or

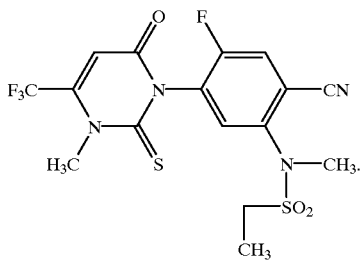

9. A process for the preparation of a compound according to claim 1, said process comprising
a) reacting an aminoalkenoic(thio) ester of the formula (II)

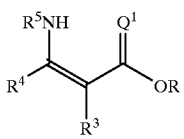

in which $Q^1$, $R^3$, $R^4$ and $R^5$ are defined in claim 1 and

R represents alkyl, with a cyanoaryl iso(thio)cyanate of the formula (III)

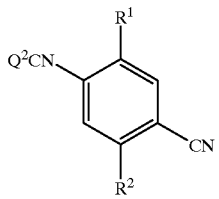

in which $Q^2$, $R^1$ and $R^2$ are defined in claim 1 in the presence or absence of a reaction auxiliary and in the presence or absence of a diluent.

10. A herbicidal or an insecticidal composition which comprises an effective amount of a compound according to claim 1, and a carrier.

11. A process for controlling undesired plants which comprises applying to said plant or to a habitat where they reside, an effective amount of a compound according to claim 1.

12. A process for controlling undesirable insects which comprises applying to said insects or to a habitat where they reside an effective amount of a compound according to claim 1.

13. A compound according to claim 1 wherein $Z=$ 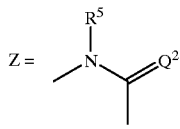

$R^1$=fluorine, chlorine, bromine or iodine;

$R^2$=fluorine, chlorine, bromine or the group —N($A^1$)SO$_2$A where

A=alkyl or cycloalkyl of up to 10 carbon atoms $A^1$=hydrogen or $C_1$ to $C_4$;

$R^3$=hydrogen;

$R^4$=haloalkyl of from 1 to 6 carbon atoms; and $R^5$=$C_1$ to $C_6$ alkyl.

* * * * *

UNITED STATES PATENT AND TRADEMARK OFFICE
CERTIFICATE OF CORRECTION

PATENT NO. : 6,339,044 B1
DATED : January 15, 2002
INVENTOR(S) : Roland Andree et al.

It is certified that error appears in the above-identified patent and that said Letters Patent is hereby corrected as shown below:

<u>Column 74,</u>
Line 56, change "unino" to -- amino --

Signed and Sealed this

Fourth Day of March, 2003

JAMES E. ROGAN
*Director of the United States Patent and Trademark Office*